United States Patent
Coller et al.

(10) Patent No.: US 11,192,889 B2
(45) Date of Patent: Dec. 7, 2021

(54) TETRAHYDRONAPHTHYRIDINEPENTAN AMIDE INTEGRIN ANTAGONISTS

(71) Applicants: The Rockefeller University, New York, NY (US); ICAHN SCHOOL OF MEDICINE AT MOUNT SINAI, New York, NY (US)

(72) Inventors: Barry S. Coller, New York, NY (US); Marta Filizola, Riverdale, NY (US); Michael Andrew Foley, New York, NY (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 180 days.

(21) Appl. No.: 16/315,093

(22) PCT Filed: Jul. 5, 2017

(86) PCT No.: PCT/US2017/040657
§ 371 (c)(1),
(2) Date: Jan. 3, 2019

(87) PCT Pub. No.: WO2018/009501
PCT Pub. Date: Jan. 11, 2018

(65) Prior Publication Data
US 2020/0181138 A1 Jun. 11, 2020

Related U.S. Application Data

(60) Provisional application No. 62/374,234, filed on Aug. 12, 2016, provisional application No. 62/358,330, filed on Jul. 5, 2016.

(51) Int. Cl.
*C07D 471/04* (2006.01)

(52) U.S. Cl.
CPC .................. *C07D 471/04* (2013.01)

(58) Field of Classification Search
CPC .... C07D 471/04; A61K 31/4375; A61P 35/00
USPC .......................................... 546/122; 514/300
See application file for complete search history.

(56) References Cited

U.S. PATENT DOCUMENTS

| | | |
|---|---|---|
| 6,784,190 B2 | 8/2004 | Askew et al. |
| 6,838,453 B2 | 1/2005 | Demassey et al. |
| 2003/0139398 A1 | 7/2003 | Hoekstra et al. |
| 2004/0038963 A1 | 2/2004 | Wang |
| 2016/0130270 A1 | 5/2016 | Askew et al. |

FOREIGN PATENT DOCUMENTS

WO  2011/011775 A1  1/2011

OTHER PUBLICATIONS

Cecil Textbook of Medicine, edited by Bennet, J.C., and Plum F., 20th edition, vol. 1, 1004-1010, 1996.*
Freshney et al., Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.Golub et al., Science, 286, 531-537, 1999.*
International Search Report and Written Opinion issued in PCT/US2017/040657, dated Sep. 29, 2017.
Extended European Search Report for PCT/US2017040657 dated Nov. 6, 2019.
Whitman, et al., Nonpeptide αvβ antagonists. Part 9: Improved pharmacokinetic profile through the use of an aliphatic, des-amide backbone, Elsevier, Science Direct, Bioorganic & Medicinal Chemistry Letters 14 (2004) 4411-4415 Feb. 23, 2004.
Brashear et al., "Non-Peptide αv β3 Antagonists. Part 5: Identification of Potent RGD Mimetics Incorporating 1-Arylβ-Amino Acids as Aspartic Acid Replacements", Bioorganic & Medicinal Chemistry Letters, vol. 12, pp. 3483-3486. 2002.
Coleman et al., "Non-Peptide αv β3 Antagonists. Part 4: Potent and Orally Bioavailable Chain-Shortened RGD Mimetics", Bioorganic & Medicinal Chemistry Letters, vol. 12, pp. 2463-2465. 2002.

\* cited by examiner

*Primary Examiner* — Tracy Vivlemore
*Assistant Examiner* — Ebenezer O Sackey
(74) *Attorney, Agent, or Firm* — Heslin Rothenberg Farley & Mesiti, P.C.

(57) ABSTRACT

Tetrahydronaphthyridines of formula

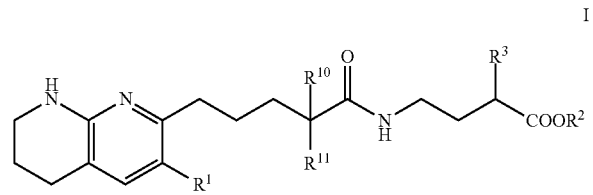

are disclosed. These compounds selectively inhibit αVβ3 without activating the αVβ3 receptor. They are useful for treating osteoporosis, acute myelogenous leukemia, sickle cell disease, focal segmental glomerulosclerosis, fibrosis, supravalvular aortic stenosis associated with Williams syndrome, tumors expressing αVβ3, tumor metastasis, bone resorption, T-cell lymphoma, retinal disease, age-related macular degeneration, diabetic retinitis, and herpes simplex virus infection. They may also be used for inhibiting tumor angiogenesis.

11 Claims, No Drawings

TETRAHYDRONAPHTHYRIDINEPENTAN AMIDE INTEGRIN ANTAGONISTS

CROSS-REFERENCE TO RELATED APPLICATIONS

This application is a U.S. National Phase filing under 35 U.S.C. § 371 of International Application PCT/US2017/040657, filed Jul. 5, 2017, and published as WO2018/009501 A1 on Jan. 11, 2018. PCT/US2017/040657 claims priority from U.S. provisional application 62/358,330, filed Jul. 5, 2016, and from U.S. provisional application 62/374,234, filed Aug. 12, 2016. Both are incorporated herein by reference in their entirety.

GOVERNMENT RIGHTS STATEMENT

This invention was made with Government support under grant HL-19278 awarded by the National Heart, Lung and Blood Institute, National Institutes of Health. The Government has certain rights in the invention.

FIELD OF THE INVENTION

The invention relates to 5-(5,6,7,8-tetrahydro-1,8-naphthyridin-2-yl)pentanamide derivatives that selectively antagonize Integrin αVβ3. These compounds are useful to treat diseases and conditions such as acute myelogenous leukemia.

BACKGROUND OF THE INVENTION

Integrin αVβ3 is widely expressed on many tissues and has been implicated in the pathogenesis of many disorders, including renal, hematologic, neoplastic, bone, and fibrotic diseases. Small molecule antagonists of αVβ3 have been developed based on the Arg-Gly-Asp (RGD) sequence found in multiple ligands, but none has been approved for clinical use. RGD-based antagonists to the αIIbβ3 receptor, which shares the same β subunit and a homologous a subunit, paradoxically activate the receptor by inducing it into a high affinity ligand binding state. The small molecule antagonists of αVβ3 and αIIbβ3 that have been used clinically to date mimic the RGD cell recognition sequence. The interaction of the Asp carboxyl in αIIbβ3 antagonists with the β3 Metal Ion-Dependent Adhesion Site (MIDAS) $Mg^{2+}$ and nearby backbone nitrogens paradoxically activates αIIbβ3 by triggering conformational changes in a key β3 loop and stabilizing a high affinity ligand binding state. This activation results in major conformational changes in the receptor (extension and swing-out) that can be detected by biophysical studies (e.g., Stokes radius, dynamic light scattering, and electron microscopy). The activation results in functional priming of the receptor so that it binds ligands spontaneously when the agent is removed by fixing and washing. In some pathological states, this activation limits the potential therapeutic efficacy of the agents since they may function as partial agonists when plasma levels drop, thus leaving the receptor in a high affinity ligand binding state. Such activation may limit the efficacy of the αIIbβ3 and αVβ3 agents reported to date. Small molecule αVβ3 antagonists that do not activate the receptor would be advantageous.

SUMMARY OF THE INVENTION

It has now been found that 5-(5,6,7,8-tetrahydro-1,8-naphthyridin-2-yl)pentanamide derivatives can antagonize Integrin αVβ3a without activating the receptor.

In one aspect, the invention relates to compounds of formula I

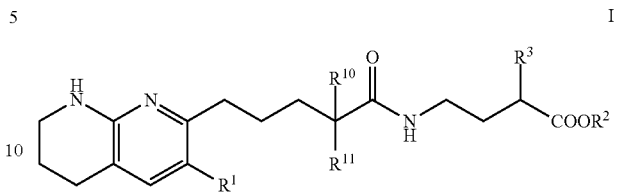

wherein
$R^1$ is hydrogen or $(C_1-C_6)$hydrocarbyl;
$R^2$ is hydrogen or $(C_1-C_6)$hydrocarbyl;
$R^3$ is chosen from —NHC(=O)$R^4$; —NHC(=O)NHR$^5$; —NHC(=O)OR$^5$; —NHSO$_2$R$^6$; —NHR$^7$; aryl and heterocyclyl; said aryl or heterocyclyl optionally substituted with one to three substituents chosen independently from $(C_1-C_{10})$hydrocarbyl, halogen, $(C_1-C_6)$haloalkyl, $(C_1-C_6)$acyl, hydroxy$(C_1-C_6)$loweralkyl, benzenesulfonyl, hydroxy, halo$(C_1-C_6)$alkoxy, $(C_1-C_6)$oxaalkyl, carboxy, $(C_1-C_6)$alkoxycarbonyl, carboxamido, cyano, acetoxy, nitro, amino, $(C_1-C_6)$alkylamino, di$(C_1-C_6)$alkylamino, $(C_1-C_6)$alkylthio, $(C_1-C_6)$alkylsulfonylamino, $(C_1-C_6)$alkylsulfinyl, $(C_1-C_6)$alkylsulfonyl, heterocyclyl, and $(C_1-C_{10})$hydrocarbyloxy;
$R^4$ is chosen from
(a) heterocyclyl optionally substituted with one to three substituents chosen independently from $(C_1-C_{10})$hydrocarbyl, halogen, $(C_1-C_6)$haloalkyl, $(C_1-C_6)$acyl, hydroxy$(C_1-C_6)$loweralkyl, benzenesulfonyl, hydroxy, halo$(C_1-C_6)$alkoxy, $(C_1-C_6)$oxaalkyl, carboxy, $(C_1-C_6)$alkoxycarbonyl, carboxamido, cyano, acetoxy, nitro, amino, $(C_1-C_6)$alkylamino, di$(C_1-C_6)$alkylamino, $(C_1-C_6)$alkylthio, $(C_1-C_6)$alkylsulfonylamino, $(C_1-C_6)$alkylsulfinyl, $(C_1-C_6)$alkylsulfonyl, heterocyclyl, and $(C_1-C_{10})$hydrocarbyloxy;
(b) $(C_1-C_{10})$hydrocarbyl;
(c) phenyl substituted with one to three substituents chosen independently from $(C_1-C_{10})$hydrocarbyl, halogen, $(C_1-C_6)$haloalkyl, $(C_1-C_6)$acyl, hydroxy$(C_1-C_6)$loweralkyl, benzenesulfonyl, hydroxy, halo$(C_1-C_6)$alkoxy, $(C_1-C_6)$oxaalkyl, carboxy, $(C_1-C_6)$alkoxycarbonyl, carboxamido, cyano, acetoxy, nitro, amino, $(C_1-C_6)$alkylamino, di$(C_1-C_6)$alkylamino, $(C_1-C_6)$alkylthio, $(C_1-C_6)$alkylsulfonylamino, $(C_1-C_6)$alkylsulfinyl, $(C_1-C_6)$alkylsulfonyl, heterocyclyl, and $(C_1-C_{10})$hydrocarbyloxy;
(d) hydroxy$(C_1-C_{10})$alkyl;
(e) $(C_1-C_{10})$oxaalkyl;
$R^5$ is chosen from $(C_1-C_{10})$hydrocarbyl; $(C_1-C_6)$oxaalkyl; $(C_1-C_{10})$fluorohydrocarbyl; aryl, heteroaryl, and benzyl; said aryl, heteroaryl or benzyl optionally substituted with one to three substituents chosen independently from $(C_1-C_{10})$hydrocarbyl, halogen, $(C_1-C_6)$haloalkyl, $(C_1-C_6)$acyl, hydroxy$(C_1-C_6)$loweralkyl, benzenesulfonyl, hydroxy, halo$(C_1-C_6)$alkoxy, $(C_1-C_6)$oxaalkyl, carboxy, $(C_1-C_6)$alkoxycarbonyl, carboxamido, cyano, acetoxy, nitro, amino, $(C_1-C_6)$alkylamino, di$(C_1-C_6)$alkylamino, $(C_1-C_6)$alkylthio, $(C_1-C_6)$alkylsulfonylamino, $(C_1-C_6)$alkylsulfinyl, $(C_1-C_6)$alkylsulfonyl, heterocyclyl, and $(C_1-C_{10})$hydrocarbyloxy;
$R^6$ is chosen from $(C_1-C_{10})$hydrocarbyl; oxo$(C_1-C_{10})$hydrocarbyl; $(C_1-C_{10})$oxaalkyl; heteroaryl; and aryl; said aryl, or heteroaryl optionally substituted with one to three substituents chosen independently from $(C_1-C_{10})$hydrocarbyl, halogen, $(C_1-C_6)$haloalkyl, $(C_1-C_6)$acyl, hydroxy $(C_1-C_6)$loweralkyl, benzenesulfonyl, hydroxy, halo$(C_1-C_6)$alkoxy, $(C_1-C_6)$oxaalkyl, carboxy, $(C_1-C_6)$alkoxycarbonyl, carboxamido, cyano, acetoxy, nitro, amino, $(C_1-C_6)$alkylamino, di$(C_1-C_6)$alkylamino, $(C_1-C_6)$alkylthio, $(C_1-C_6)$alkylsulfonylamino, $(C_1-C_6)$alkylsulfinyl, $(C_1-C_6)$alkylsulfonyl, heterocyclyl, and $(C_1-C_{10})$hydrocarbyloxy; and $R^7$ is chosen from heteroaryl; and aryl; said aryl, or heteroaryl optionally substituted with one to three substituents chosen independently from $(C_1-C_{10})$hydrocarbyl, halogen, $(C_1-C_6)$haloalkyl, $(C_1-C_6)$acyl, hydroxy$(C_1-C_6)$loweralkyl, benzenesulfonyl, hydroxy, halo$(C_1-C_6)$alkoxy, $(C_1-C_6)$oxaalkyl, carboxy, $(C_1-C_6)$alkoxycarbonyl, carboxamido, cyano, acetoxy, nitro, amino, $(C_1-C_6)$alkylamino, di$(C_1-C_6)$alkylamino, $(C_1-C_6)$alkylthio, $(C_1-C_6)$alkylsulfonylamino, $(C_1-C_6)$alkylsulfinyl, $(C_1-C_6)$alkylsulfonyl, heterocyclyl, and $(C_1-C_{10})$hydrocarbyloxy and $R^{10}$ and $R^{11}$ are chosen independently from hydrogen and fluoro.

In another aspect, the invention relates to methods for treating osteoporosis, acute myelogenous leukemia, sickle cell disease, focal segmental glomerulosclerosis, herpes simplex virus infection, supravalvular aortic stenosis associated with Williams syndrome, bone resorption, tumors expressing αVβ3, tumor metastasis, T-cell lymphoma, retinal disease, age-related macular degeneration, diabetic retinitis, and fibrosis comprising administering a compound of formula I.

In another aspect, the invention relates to a method for inhibiting tumor angiogenesis comprising administering a compound of formula I.

In another aspect, the invention relates to pharmaceutical compositions comprising a pharmaceutically acceptable carrier and a compound of formula I.

DETAILED DESCRIPTION OF THE INVENTION

In one aspect, the invention relates to compounds of formula I:

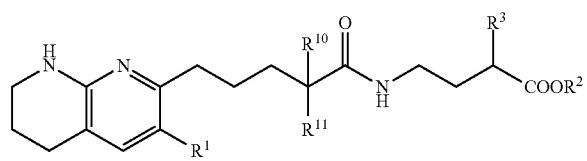

I

In these compounds, $R^1$ and $R^2$ may be hydrogen or $(C_1-C_6)$hydrocarbyl. In some embodiments, $R^1$ is hydrogen; in some $R^1$ is cyclopropyl. In some embodiments, $R^2$ is hydrogen; in some $R^2$ is methyl.

$R^3$ may be chosen from —NHC(=O)$R^4$; —NHC(=O)NHR$^5$; —HC(=O)OR$^5$; —NHSO$_2$R$^6$; —NHR$^7$; aryl; and heterocyclyl. The aryl or heterocyclyl residues may be optionally substituted with one to three substituents chosen independently from $(C_1-C_{10})$hydrocarbyl, halogen, $(C_1-C_6)$haloalkyl, $(C_1-C_6)$acyl, hydroxy$(C_1-C_6)$loweralkyl, benzenesulfonyl, hydroxy, halo$(C_1-C_6)$alkoxy, $(C_1-C_6)$oxaalkyl, carboxy, $(C_1-C_6)$alkoxycarbonyl, carboxamido, cyano, acetoxy, nitro, amino, $(C_1-C_6)$alkylamino, di$(C_1-C_6)$alkylamino, $(C_1-C_6)$alkylthio, $(C_1-C_6)$alkylsulfonylamino, $(C_1-C_6)$alkylsulfinyl, $(C_1-C_6)$alkylsulfonyl, heterocyclyl, and $(C_1-C_{10})$hydrocarbyloxy.

In one embodiment, $R^3$ is chosen from —NHC(=O)$R^4$; —NHC(=O)NHR$^5$; —NHC(=O)OR$^5$; —NHSO$_2$R$^6$; —NHR$^7$; phenyl and heterocyclyl, optionally substituted with $(C_1-C_{10})$hydrocarbyl or $(C_1-C_{10})$hydrocarbyloxy;

$R^4$ is chosen from
(a) heterocyclyl optionally substituted with $(C_1-C_6)$hydrocarbyl or $(C_1-C_6)$hydrocarbyloxy;
(b) $(C_1-C_{10})$hydrocarbyl;
(c) phenoxyphenyl;
(d) hydroxy$(C_1-C_6)$alkyl; and
(e) $(C_1-C_6)$oxaalkyl;

$R^5$ is chosen from $(C_1-C_{10})$hydrocarbyl; $(C_1-C_6)$oxaalkyl; $(C_1-C_{10})$fluorohydrocarbyl; and methoxybenzyl;

$R^6$ is chosen from $(C_1-C_{10})$hydrocarbyl; pyridinyl; phenoxyphenyl; $(C_1-C_6)$oxaalkyl; and camphoryl; and $R^7$ is heterocyclyl optionally substituted with $(C_1-C_6)$hydrocarbyl or $(C_1-C_6)$hydrocarbyloxy.

In one embodiment, in which $R^3$ is —NHC(=O)$R^4$, $R^4$ is chosen from 2-methoxyethyl, hydroxy$(C_1-C_6)$alkyl, phenyl, heteroaryl, and naphthyl. The phenyl, heteroaryl, or naphthyl residues may be optionally substituted with one or two $(C_1-C_4)$hydrocarbyl, methoxy, or phenyl substituents. In another embodiment, $R^4$ is chosen from phenyl, 4-pyridinyl, 3-pyridinyl, 2-pyridinyl, 1-naphthyl, 2-naphthyl, 2-methoxyethyl, hydroxymethyl, 2,6-dimethylphenyl, 6-methoxypyridin-2-yl, 5-phenylthiazol-2-yl, 1-(cyclopropylmethyl)benzimidazol-2-yl, benzoxazol-2-yl, and benzothiazol-2-yl.

In one embodiment, in which $R^3$ is —NHC(=O)NHR$^5$, $R^5$ is chosen from $(C_1-C_6)$hydrocarbyl; $(C_1-C_6)$oxaalkyl; and aryl. In another embodiment, $R^5$ is chosen from ethyl, 2-methoxyethyl, and 1-naphthyl.

In one embodiment, in which $R^3$ is —NHC(=O)OR$^5$, $R^5$ is chosen from benzyl, $(C_1-C_6)$hydrocarbyl, methoxybenzyl, phenethyl, fluoro$(C_1-C_{10})$hydrocarbyl, and fluorobenzyl. In another embodiment, $R^5$ is chosen from benzyl, methyl, isopropyl, isobutyl, p-methoxybenzyl, o-methoxybenzyl, phenethyl, pentafluoropropyl, (4,4-difluorocyclohexyl)methyl, o-fluorobenzyl, m-fluorobenzyl, p-fluorobenzyl, and 3,4-difluorobenzyl.

In one embodiment, in which $R^3$ is —NHSO$_2$R$^6$, $R^6$ is chosen from benzyl, $(C_1-C_6)$hydrocarbyl, phenethyl, 2-methoxyethyl, heteroaryl, naphthyl, camphoryl, and phenyl substituted with phenoxy or methyl. In another embodiment, $R^6$ is chosen from p-tolyl, benzyl, isobutyl, phenethyl, 2-methoxyethyl, 3-pyridinyl, 2-naphthyl, 1-naphthyl, 3-phenoxyphenyl, 2,4,6-trimethylphenyl, and camphoryl.

In one embodiment, in which $R^3$ is —NHR$^7$, $R^7$ is heteroaryl optionally substituted with $(C_1-C_6)$hydrocarbyl. In another embodiment, $R^7$ is chosen from benzoxazol-2-yl, benzothiazol-2-yl, and 5-phenylpyrimidin-2-yl.

In one embodiment, in which $R^3$ is heteroaryl or aryl (optionally substituted with $(C_1-C_6)$hydrocarbyl or phenoxy), $R^3$ is chosen from phenyl, 4-phenyl-1,2,3-triazol-1-yl, 4-isobutyl-1,2,3-triazol-1-yl, 3-phenyl-1,2,4-triazol-1-yl, 6-methoxypyridin-3-yl, 6-phenoxypyridin-3-yl, and quinolin-3-yl.

In some embodiments, $R^{10}$ and $R^{11}$ are both hydrogen. In some embodiments one or both of $R^{10}$ and $R^{11}$ are fluoro Throughout this specification the terms and substituents retain their definitions.

$C_1$ to $C_{10}$ hydrocarbon includes alkyl, cycloalkyl, polycycloalkyl, alkenyl, alkynyl, aryl and combinations thereof.

Examples include benzyl, phenethyl, cyclohexylmethyl, adamantyl, camphoryl and naphthylethyl. Hydrocarbyl refers to any substituent comprised of hydrogen and carbon as the only elemental constituents. Aliphatic hydrocarbons are hydrocarbons that are not aromatic; they may be saturated or unsaturated, cyclic, linear or branched. Examples of aliphatic hydrocarbons include isopropyl, 2-butenyl, 2-butynyl, cyclopentyl, norbornyl, etc. Aromatic hydrocarbons include benzene (phenyl), naphthalene (naphthyl), anthracene, etc.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include cyclopropyl, cyclobutyl, cyclopentyl, norbornyl and the like.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene and cyclohexene; ($C_8$-$C_{12}$) carbopolycycle refers to such systems as norbornane, decalin, indane and naphthalene. Carbocycle, if not otherwise limited, refers to monocycles, bicycles and polycycles.

Heterocycle means an aliphatic or aromatic carbocycle residue in which from one to four carbons is replaced by a heteroatom selected from the group consisting of N, O, and S. The nitrogen and sulfur heteroatoms may optionally be oxidized, and the nitrogen heteroatom may optionally be quaternized. Unless otherwise specified, a heterocycle may be non-aromatic (heteroaliphatic) or aromatic (heteroaryl). Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, benzoxazolyl, tetrahydrofuryl, tetrahydropyranyl, thienyl (also historically called thiophenyl), benzothienyl, thiamorpholinyl, oxadiazolyl, triazolyl and tetrahydroquinolinyl.

Hydrocarbyloxy refers to groups of from 1 to 20 carbon atoms, preferably 1 to 10 carbon atoms, more preferably 1 to 6 carbon atoms attached to the parent structure through an oxygen. Alkoxy is a subset of hydrocarbyloxy and includes groups of a straight or branched configuration. Examples include methoxy, ethoxy, propoxy, isopropoxy and the like. Lower-alkoxy refers to groups containing one to four carbons. The term "halogen" means fluorine, chlorine, bromine or iodine atoms.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. Lower-acyl refers to groups containing one to four carbons. The double bonded oxygen, when referred to as a substituent itself is called "oxo".

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxy lower alkyl, carbonyl, phenyl, heteroaryl, benzenesulfonyl, hydroxy, lower alkoxy, haloalkoxy, oxaalkyl, carboxy, alkoxycarbonyl [—C(=O)O-alkyl], alkoxycarbonylamino [HNC(=O)O-alkyl], aminocarbonyl (also known as carboxamido) [—C(=O)NH$_2$], alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkyl sulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl), whereas on others (e.g. camphor) it will be appropriate. In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine. Preferred substituents are halogen, ($C_1$-$C_4$)alkyl, ($C_1$-$C_4$)alkoxy, ($C_1$-$C_4$)fluoroalkyl, ($C_1$-$C_4$)fluoroalkoxy, hydroxy, amino, ($C_1$-$C_4$)alkylamino, di($C_1$-$C_4$)alkylamino, ($C_1$-$C_4$)acylamino, ($C_1$-$C_4$)fluoroalkyl and ($C_1$-$C_4$)fluoroalkoxy.

Substituents R" are generally defined when introduced and retain that definition throughout the specification and in all independent claims.

Preparation of compounds can involve the protection and deprotection of various chemical groups. The need for protection and deprotection, and the selection of appropriate protecting groups, can be readily determined by one skilled in the art. Suitable groups for that purpose are discussed in standard textbooks in the field of chemistry, such as Protective Groups in Organic Synthesis by T. W. Greene and P. G. M. Wuts [John Wiley & Sons, New York, 1999], in *Protecting Group Chemistry*, 1$^{st}$ Ed., Oxford University Press, 2000; and in *March's Advanced Organic chemistry: Reactions, Mechanisms, and Structure*, 5$^{th}$ Ed., Wiley-Interscience Publication, 2001.

The compounds described herein will, in almost all instances, contain an asymmetric center and may thus give rise to enantiomers, diastereomers, and other stereoisomeric forms which may be defined in terms of absolute stereochemistry as (R)- or (S)-. The present invention is meant to include all such possible isomers as racemates, optically pure forms and intermediate mixtures. Optically active (R)- and (S)-isomers may be prepared using homo-chiral synthons or homo-chiral reagents, or optically resolved using conventional techniques. All tautomeric forms are intended to be included. The graphic representations of racemic, ambiscalemic and scalemic or enantiomerically pure compounds used herein are taken from Maehr *J. Chem. Ed.* 62, 114-120 (1985): simple, single bond lines convey connectivity only and no stereochemical implication; solid and broken wedges are used to denote the absolute configuration of a chiral element; wavy lines indicate explicit disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. Enantiomerically pure means greater than 80 ee and preferably greater than 90 ee.

As used herein, the terms "treatment" or "treating," or "palliating" or "ameliorating" refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological systems associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological systems of a disease, even though a diagnosis of this disease may not have been made. For example, treating osteoporosis may involve administering the compounds to a patient at risk of developing osteoporosis to diminish the likelihood and/or severity of the condition.

As used herein, and as would be understood by the person of skill in the art, the recitation of "a compound"—unless expressly further limited—is intended to include salts of that compound. In a particular embodiment, the term "compound of formula" refers to the compound or a pharmaceutically acceptable salt thereof.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

Also provided herein is a pharmaceutical composition comprising a compound disclosed above, or a pharmaceutically acceptable salt form thereof, and a pharmaceutically acceptable carrier or diluent.

While it may be possible for the compounds of formula I to be administered as the raw chemical, it is preferable to present them as a pharmaceutical composition. According to a further aspect, the present invention provides a pharmaceutical composition comprising a compound of formula I or a pharmaceutically acceptable salt thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula I or a pharmaceutically acceptable salt thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

In general, compounds of formula I can be prepared as described below.

Abbreviations
Ac=acetyl
aq.=aqueous
Bu=butyl
DIAD=diisopropyl azodicarboxylate
DIPEA=diisopropylethylamine, Hünig's base
DMF=N,N-dimethylformamide
DMSO=dimethyl sulfoxide
EtOAc=ethyl acetate
Et=ethyl
HATU=1-[bis(dimethylamino)methylene]-1H-1,2,3-triazolo[4,5-b]pyridinium 3-oxid hexafluorophosphate
HOBt=1-hydroxybenzotriazole
HPLC=high-performance liquid chromatography
Me=methyl
PE=petroleum ether
rt=room temperature
sat.=saturated
t- or tert-=tertiary
TEA=triethanolamine
TFA=trifluoroacetic acid
THF=tetrahydrofuran
TLC=thin layer chromatography
TMS=trimethylsilyl
WSC=Water soluble carbodiimide, 1-ethyl-3-(3-dimethylaminopropyl) carbodiimide Solvents and reagents were purchased from VWR or Sigma Aldrich. All reactions involving air- or moisture-sensitive compounds were performed under nitrogen atmosphere using dried glassware. $^1$H NMR spectra were recorded at 500 MHz and 125 Mz, respectively, on a Bruker Advance III HD 500 MHz NMR spectrometer equipped with a TCI cryogenic probe with enhanced $^1$H and $^{13}$C detection. All data was collected at 298 K, and signals were reported in parts per million (ppm), internally referenced for $^1$H and $^{13}$C to chloroform signal at 7.26 ppm or 77.0 ppm, to DMSO signal at 2.50 ppm or 39.5 ppm, or to TMS at 0 ppm. Chemical shifts are reported in ppm and the coupling constants (J) are expressed in hertz (Hz). Splitting patterns are designated as follows: s, singlet; d, doublet; t, triplet; q, quartet; m, multiplet; dd, doublet of doublets; ddd, doublet of doublets of doublets; dt, doublet of triplets. Flash chromatography purifications were performed on CombiFlash Rf (TELEDYNE ISCO) as the stationary phase. Purity for all tested compounds was determined through high-performance liquid chromatography and all compounds were found to be >95% pure.

EXAMPLE A

Ethyl 3-[5-(5,6,7,8-tetrahydro-1,8-naphthyridin-2-yl)pentanoylamino]propanoate: To a solution of 5-(5,6,7,8-tetrahydro-1,8-naphthyridin-2-yl)pentanoic acid (60.00 mg, 256.09 umol), 1-hydroxybenzotriazole dihydrate (56.98 mg, 332.92 umol) and 3-(ethyliminomethyleneamino)-N,N-dimethyl-propan-1-amine;hydrochloride (63.82 mg, 332.92 umol) in DMF (3.00 mL) was added triethylamine (77.74 mg, 768.28 μmol) at room temperature. After stirring for 10 min, ethyl 3-aminopropanoate (47.21 mg, 307.31 μmol) in DMF (1 mL) was added to the reaction mixture. The mixture was stirred at room temperature overnight. The mixture was quenched with water, sat.NaHCO$_3$ aq. and brine, dried over MgSO$_4$ and concentrated in vacuo. The residue (diluted with CH$_2$Cl$_2$) was purified by NH-silica gel chromatography (EtOAc:MeOH=0-10%) to give ethyl 3-[5-(5,6,7,8-tetrahydro-1,8-naphthyridin-2-yl)pentanoylamino]propanoate (54.00 mg, 161.96 umol, 63.24% yield) as a colorless solid. $^1$H NMR (500 MHz, Chloroform-d) δ 7.04 (dd, J=6.9, 1.4 Hz, 1H), 6.33 (d, J=7.3 Hz, 1H), 6.11 (s, 1H), 4.78 (s, 1H), 4.15 (q, J=7.1 Hz, 2H), 3.50 (q, J=6.1 Hz, 2H), 3.39 (dt, J=5.6, 2.6 Hz, 2H), 2.68 (t, J=6.3 Hz, 2H), 2.57-2.45 (m, 4H), 2.17 (td, J=5.9, 4.9, 3.3 Hz, 2H), 1.94-1.84 (m, 2H), 1.67 (d, J=3.8 Hz, 4H), 1.26 (t, J=7.1 Hz, 3H). MS m/z: 334 [M+H]$^+$.

3-[5-(5,6,7,8-Tetrahydro-1,8-naphthyridin-2-yl)pentanoylamino]propanoic acid: The mixture of ethyl 3-[5-(5,6,7,8-tetrahydro-1,8-naphthyridin-2-yl)pentanoylamino]propanoate (54.00 mg, 161.96 umol) and sodium;hydroxide (1 M, 323.92 uL) in THF (2.00 mL)/EtOH (2.00 mL) was stirred at room temperature overnight. The mixture was neutralized to pH 7 and concentrated in vacuo. The residue (diluted with CH$_3$CN:water=1:1) was purified by reversed phase chromatography (water:CH$_3$CN=0-20%) to give 3-[5-(5,6,7,8-tetrahydro-1,8-naphthyridin-2-yl)pentanoylamino]propanoic acid Example A (23.00 mg, 75.32 umol, 46.50% yield) as a white amorphous solid. $^1$H NMR (500 MHz, DMSO-d$_6$) δ 7.83 (t, J=5.6 Hz, 1H), 7.01 (d, J=7.2 Hz, 1H), 6.28 (s, 1H), 6.23 (d, J=7.2 Hz, 1H), 3.17-3.25 (m, 4H), 2.59 (t, J=6.2 Hz, 2H), 2.40 (t, J=7.3 Hz, 2H), 2.32 (t, J=6.9 Hz, 2H), 2.04 (t, J=7.2 Hz, 2H), 1.78-1.71 (m, 2H), 1.56-1.41 (m, 4H), offset (1COOH). MS m/z: 306 [M+H]$^+$.

EXAMPLE 1

General Procedure for the Parallel Syntheses of Example 1 and Example B

To a solution of compound 5-(5,6,7,8-tetrahydro-1,8-naphthyridin-2-yl)pentanoic acid (0.023 g, 100 umol) in CH$_2$Cl$_2$ (1 mL) were added ethyl 4-aminobutyrate (200 μmol) or ethyl 5-aminopentanoate, 1-(3-dimethylaminopropyl)-3-ethylcarbodiimide hydrochloride (0.038 g, 200 umol) and HOBt hydrate (0.031 g, 200 umol). The mixture was stirred at rt overnight, then poured into EtOAc (3 mL) and water (1 mL) and stirred for 5 min. The organic layer was evaporated by blowing away with air at 60° C. The residue was purified by preparative HPLC (YMC-Triart C18, eluted with MeCN/10 mM NH$_4$HCO$_3$ aq.). The desired fraction was evaporated by blowing away with air at 60° C. To the residue was added THF (500 uL) and 1N NaOH (500 uL). The mixture was stirred at rt overnight, then 1N HCl (500 uL) was added to the reaction mixture. The residue was purified by preparative HPLC (YMC-Triart C18, eluted with MeCN/10 mM NH$_4$HCO$_3$ aq.). The desired fraction was evaporated by blowing away with air at 60° C. to give the desired product.

Example 1: 4-[5-(5,6,7,8-tetrahydro-1,8-naphthyridin-2-yl)pentanoylamino]butanoic acid. $^1$H NMR (500 MHz, DMSO-d$_6$) δ 12.15 (brs, 1H), 7.81(s, 1H), 7.08(d, J=6.9 Hz, 1H), 6.36(s, 1H), 6.28 (d, J=6.9 Hz 1H), 3.31-3.22 (m, 2H), 3.09-3.01 (m, 2H), 2.63 (t, J=4.3 Hz, 2H), 2.45 (t, J=6.6 Hz, 2H), 2.23 (t, J=7.1 Hz, 2H), 2.08 (t, J=7.1 Hz, 2H), 1.82-1.74 (m, 2H), 1.67-1.45 (m, 6H). MS m/z: 320 [M+H]$^+$.

Example B: 5-[5-(5,6,7,8-tetrahydro-1,8-naphthyridin-2-yl)pentanoylamino]pentanoic acid. MS m/z: 334 [M+H]$^+$.

PREPARATION OF EXAMPLES 2-7

Methyl (2S)-2-(benzyloxycarbonylamino)-4-[5-(5,6,7,8-tetrahydro-1,8-naphthyridin-2-yl)pentanoylamino]butanoate Example 2

To a solution of 5-(5,6,7,8-tetrahydro-1,8-naphthyridin-2-yl)pentanoic acid (750.00 mg, 3.20 mmol), 3-(ethyliminomethyleneamino)-N,N-dimethyl-propan-1-amine;hydrochloride (1.19 g, 6.21 mmol), 1-hydroxybenzotriazole; dihydrate (1.06 g, 6.21 mmol) and Triethylamine (1.26 g, 12.43 mmol, 1.72 mL) in DMF (5.00 mL) was added methyl (2S)-4-amino-2-(benzyloxycarbonylamino)butanoate hydrochloride (1.03 g, 3.42 mmol) at room temperature. The mixture was stirred at room temperature overnight. The mixture was quenched with water, diluted with EtOAc, washed with water, brine, dried with $MgSO_4$ and concentrated in vacuo. The residue was purified by chromatography silica gel (hexane:EtOAc=10-100%, EtOAc:MeOH=0-20%) to give methyl (2S)-2-(benzyloxycarbonylamino)-4-[5-(5,6,7,8-tetrahydro-1,8-naphthyridin-2-yl)pentanoylamino]butanoate Example 2 (1.07 g, 2.22 mmol, 71.46% yield) as a white solid. MS m/z: 483 $[M+H]^-$.

(2S)-2-(Benzyloxycarbonylamino)-4-[5-(5,6,7,8-tetrahydro-1,8-naphthyridin-2-yl)pentanoylamino]butanoic acid Example 3

To a solution of Example 2 (750.00 mg, 3.20 mmol)5-(5,6,7,8-tetrahydro-1,8-naphthyridin-2-yl)pentanoic acid (750.00 mg, 3.20 mmol), 3-(ethyliminomethyleneamino)-N,N-dimethyl-propan-1-amine;hydrochloride (1.19 g, 6.21 mmol), 1-hydroxybenzotriazole;dihydrate (1.06 g, 6.21 mmol) and 3-(ethyliminomethyleneamino)-N,N-dimethyl-propan-1-amine;hydrochloride (1.19 g, 6.21 mmol) Triethylamine (1.26 g, 12.43 mmol, 1.72 mL) in DMF (5.00 mL) was added methyl (2S)-4-amino-2-(benzyloxycarbonylamino)butanoate (1.03 g, 3.42 mmol, CL) at room temperature. The mixture was stirred at room temperature overnight. The mixture was quenched with water, diluted with EtOAc, washed with water, brine, dried with $MgSO_4$ and concentrated in vacuo. The residue was purified by chromatography silica gel (hexane:EtOAc=10-100%, EtOAc:MeOH=0-20%) to give methyl (2S)-2-(benzyloxycarbonylamino)-4-[5-(5,6,7,8-tetrahydro-1,8-naphthyridin-2-yl)pentanoylamino]butanoate Example 3 (1.07 g, 2.22 mmol, 71.46% yield) as a white solid. MS m/z: 469 $[M+H]^+$.

(2R)-2-(Benzyloxycarbonylamino)-4-[5-(5,6,7,8-tetrahydro-1,8-naphthyridin-2-yl)pentanoylamino]butanoic acid Example 4

A mixture of example 6 (62.00 mg, 128.48 umol) and 1 M NaOH (3.00 mL) in THF/MeOH (3.00 mL) was stirred at room temperature for 1 h. The mixture was neutralized with 1 M HCl and concentrated in vacuo. The residue was purified by silica gel column chromatography (10-60% MeOH in EtOAc) to give (2R)-2-(benzyloxycarbonylamino)-4-[5-(5,6,7,8-tetrahydro-1,8-naphthyridin-2-yl)pentanoylamino]butanoic acid Example 4 (18.00 mg, 38.42 umol, 29.90% yield) as a white solid. MS m/z: 469 $[M+H]^+$.

Methyl 2-(benzyloxycarbonylamino)-4-[5-(5,6,7,8-tetrahydro-1,8-naphthyridin-2-yl)pentanoylamino]butanoate Example 5

To a solution of 5-(5,6,7,8-tetrahydro-1,8-naphthyridin-2-yl)pentanoic acid (2.80 g, 11.95 mmol), 3-(ethyliminomethyleneamino)-N,N-dimethyl-propan-1-amine hydrochloride (4.58 g, 23.90 mmol), 1-hydroxybenzotriazole dihydrate (4.09 g, 23.90 mmol) and DIPEA (6.18 g, 47.80 mmol, 8.35 mL) in DIVIF (50.00 mL) was added methyl 4-amino-2-(benzyloxycarbonylamino)butanoate hydrochloride (3.62 g, 11.95 mmol) at room temperature. The mixture was stirred at room temperature overnight. The mixture was quenched with water, diluted with EtOAc, washed with water, brine, dried with $MgSO_4$ and concentrated in vacuo. The residue was purified by chromatography on silica gel (hexane:EtOAc=10-100%, EtOAc:MeOH=0-20%) to give methyl 2-(benzyloxycarbonylamino)-4-[5-(5,6,7,8-tetrahydro-1,8-naphthyridin-2-yl)pentanoylamino]butanoate (4.14 g, 8.58 mmol, 71.79% yield) as a white solid. MS m/z: 483 $[M+H]^+$.

Methyl (2R)-2-(benzyloxycarbonylamino)-4-[5-(5,6,7,8-tetrahydro-1,8-naphthyridin-2-yl)pentanoylamino]butanoate Example 6

To a solution of 5-(5,6,7,8-tetrahydro-1,8-naphthyridin-2-yl)pentanoic acid (350.00 mg, 1.49 mmol), 3-(ethyliminomethyleneamino)-N,N-dimethyl-propan-1-amine hydrochloride (572.75 mg, 2.99 mmol), 1-hydroxybenzotriazole dihydrate (511.35 mg, 2.99 mmol) and DIPEA (772.27 mg, 5.98 mmol, 1.04 mL) in DMF (5.00 mL) was added methyl (2R)-4-amino-2-(benzyloxycarbonylamino)butanoate hydrochloride (452.27 mg, 1.49 mmol) at room temperature. The mixture was stirred at room temperature overnight. The mixture was quenched with water, diluted with EtOAc, washed with water, brine, dried with $MgSO_4$ and concentrated in vacuo. The residue was purified by silica gel chromatography (hexane:EtOAc=10-100%, EtOAc:MeOH=0-20%) and recrystallized with EtOAc/MeOH to give methyl (2R)-2-(benzyloxycarbonylamino)-4-[5-(5,6,7,8-tetrahydro-1,8-naphthyridin-2-yl)pentanoylamino]butanoate Example 6 (400.00 mg, 828.90 umol, 55.63% yield) as a white solid. MS m/z: 483 $[M+H]^-$.

2-(Benzyloxycarbonylamino)-4-[5-(5,6,7,8-tetrahydro-1,8-naphthyridin-2-yl)pentanoylamino]butanoic acid Example 7

To a mixture of Example 5 (160.00 mg, 331.56 umol), $H_2O$ (1.50 mL), and THF (6.00 mL) was added lithium hydroxide monohydrate (69.56 mg, 1.66 mmol) at room temperature. After being stirred for 5 h, 1N HCl (1.0 M, 1.66 mL) was added to the reaction mixture. The mixture was concentrated in vacuo. The residue was purified by column chromatography on silica (60%-100% EtOAc in hexane, then 0%-30% MeOH in EtOAc) to give a white solid. The obtained solid was washed with EtOAc to give 2-(benzyloxycarbonylamino)-4-[5-(5,6,7,8-tetrahydro-1,8-naphthyridin-2-yl)pentanoylamino]butanoic acid Example 7 (93.60 mg, 199.77 umol, 60.25% yield) as a white solid. 1H NMR (500 MHz, DMSO-d6) δ 7.84 (t, J=5.5 Hz, 1H), 7.58 (d, J=8.0 Hz, 1H), 7.42-7.30 (m, 5H), 7.05 (d, J=7.2 Hz, 1H), 6.46 (s, 1H), 6.27 (d, J=7.2 Hz, 1H), 5.09-5.00 (m, 2H), 4.02-3.96 (m, 1H), 3.28-3.22 (m, 2H), 3.17-3.03 (m, 2H), 2.62 (t, J=6.3 Hz, 2H), 2.43 (t, J=7.3 Hz, 2H), 2.07 (t, J=7.0 Hz, 2H), 1.92-1.83 (m, 1H), 1.79-1.66 (m, 3H), 1.59-1.45 (m, 4H), 1H not found. MS m/z: 469 $[M+H]^+$.

PREPARATION OF EXAMPLES 8-13

Methyl 2-phenyl-4-[5-(5,6,7,8-tetrahydro-1,8-naphthyridin-2-yl)pentanoylamino]butanoate Example 8

A mixture of 5-(5,6,7,8-tetrahydro-1,8-naphthyridin-2-yl)pentanoic acid hydrochloride (207.45 mg, 766.22 μmol), methyl 4-amino-2-phenyl-butanoate hydrochloride (160.00 mg, 696.56 µmol), HOBt (141.18 mg, 835.87 µmol, 80% purity), triethylamine (281.94 mg, 2.79 mmol, 386.22 µL) and 3-(ethyliminomethyleneamino)-N,N-dimethylpropan-1-amine hydrochloride (160.24 mg, 835.87 µmol) in DMF (5.00 mL) was stirred at room temperature overnight. The mixture was diluted with water and extracted with EtOAc. The organic layer was washed with NaHCO$_3$ aq. and brine, dried over MgSO$_4$ and concentrated in vacuo. The residue was purified by silica gel column chromatography (0-20% MeOH in EtOAc) to give methyl 2-phenyl-4-[5-(5,6,7,8-tetrahydro-1,8-naphthyridin-2-yl)pentanoylamino]butanoate (238.00 mg, 581.17 µmol, 83.43% yield) as a white amorphous solid. MS m/z: 410 [M+H]$^+$.

2-Phenyl-4-[5-(5,6,7,8-tetrahydro-1,8-naphthyridin-2-yl)pentanoylamino]butanoic acid Example 9

A mixture of Example 8 (238.00 mg, 581.17 µmol) and 1 M NaOH (5.00 mL) in THF/MeOH (5.00 mL) was stirred at room temperature for 2 h. The mixture was neutralized with 1 M HCl aq. and concentrated in vacuo. The residue was purified by silica gel column chromatography (0-30% MeOH in EtOAc) to give 2-phenyl-4-[5-(5,6,7,8-tetrahydro-1,8-naphthyridin-2-yl)pentanoylamino]butanoic acid (170.00 mg, 429.85 µmol, 73.96% yield) as a white solid. MS m/z: 396 [M+H]$^+$.

Methyl 2-methyl-4-[5-(5,6,7,8-tetrahydro-1,8-naphthyridin-2-yl)pentanoylamino]butanoate Example 10

A mixture of 5-(5,6,7,8-tetrahydro-1,8-naphthyridin-2-yl)pentanoic acid hydrochloride (177.67 mg, 656.21 µmol), methyl 4-amino-2-methyl-butanoate hydrochloride (100.00 mg, 596.55 µmol), HOBt (120.91 mg, 715.86 µmol, 80% purity), triethylamine (241.46 mg, 2.39 mmol, 330.77 µL) and 3-(ethyliminomethyleneamino)-N,N-dimethyl-propan-1-amine hydrochloride (137.23 mg, 715.86 µmol) in DIVIF (5.00 mL) was stirred at room temperature overnight. The mixture was diluted with water and extracted with EtOAc. The organic layer was washed with NaHCO$_3$ aq. and brine, dried over MgSO$_4$ and concentrated in vacuo. The residue was purified by silica gel column chromatography (0-20% MeOH in EtOAc) to give methyl 2-methyl-4-[5-(5,6,7,8-tetrahydro-1,8-naphthyridin-2-yl)pentanoylamino]butanoate (100.00 mg, 287.81 µmol, 48.25% yield) as a white amorphous solid. MS m/z: 348 [M+H]$^+$.

Methyl 2-benzyl-4-[5-(5,6,7,8-tetrahydro-1,8-naphthyridin-2-yl)pentanoylamino]butanoate Example 11

A mixture of 5-(5,6,7,8-tetrahydro-1,8-naphthyridin-2-yl)pentanoic acid hydrochloride (122.19 mg, 451.32 µmol), methyl 4-amino-2-benzyl-butanoate hydrochloride (100.00 mg, 410.29 µmol), HOBt (83.16 mg, 492.35 umol, 80% purity), triethylamine (166.07 mg, 1.64 mmol, 227.49 µL) and 3-(ethyliminomethyleneamino)-N,N-dimethyl-propan-1-amine hydrochloride (94.38 mg, 492.35 umol) in DMF (5.00 mL) was stirred at room temperature overnight. The mixture was diluted with water and extracted with EtOAc. The organic layer was washed with NaHCO$_3$ aq. and brine, dried over MgSO$_4$ and concentrated in vacuo. The resodue was purified by silica gel column chromatography (0-20% MeOH in EtOAc) to give methyl 2-benzyl-4-[5-(5,6,7,8-tetrahydro-1,8-naphthyridin-2-yl)pentanoylamino]butanoate (139.00 mg, 328.18 µmol, 79.99% yield) as a white amorphous solid. MS m/z: 424 [M+H]$^+$.

2-Methyl-4-[5-(5,6,7,8-tetrahydro-1,8-naphthyridin-2-yl)pentanoylamino]butanoic acid Example 12

A mixture of Example 10 (100.00 mg, 287.81 umol) and 1 M NaOH (5.00 mL) in THF/MeOH (5.00 mL) was stirred at room temperature for 5 h. The mixture was neutralized with 1 M HCl aq. and concentrated in vacuo. The residue was purified by silica gel column chromatography (10-30% MeOH in EtOAc) to give 2-methyl-4-[5-(5,6,7,8-tetrahydro-1,8-naphthyridin-2-yl)pentanoylamino]butanoic acid (20.00 mg, 59.98 umol, 20.84% yield) as a white solid. MS m/z: 334 [M+H]$^+$.

2-Benzyl-4-[5-(5,6,7,8-tetrahydro-1,8-naphthyridin-2-yl)pentanoylamino]butanoic acid Example 13

A mixture of Example 11 (100.00 mg, 236.10 µmol) in 3 M HCl aq. (236.10 i.tmol, 10.00 mL) was stirred at 40° C. for 2 d. The mixture was neutralized with 1 M NaOH aq. and concentrated in vacuo. The residue was purified by silica gel column chromatography (0-30% MeOH in EtOAc) to give 2-benzyl-4-[5-(5,6,7,8-tetrahydro-1,8-naphthyridin-2-yl) pentanoylamino]butanoic acid (55.00 mg, 134.30 umol, 56.88% yield) as a white amorphous solid. MS m/z: 334 [M+H]$^-$.

Preparation of 2-(p-Tolylsulfonylamino)-4-[5-(5,6,7, 8-tetrahydro-1,8-naphthyridin-2-yl)pentanoylamino] butanoic acid Example 14

Methyl 2-amino-4-[5-(5,6,7,8-tetrahydro-1,8-naphthyridin-2-yl)pentanoylamino]butanoate The mixture of Example 5 (2.43 g, 5.04 mmol) and Pd/C (250.00 mg, 2.06 mmol) in MeOH (25.00 mL) was stirred under H$_2$ atmosphere (1 atm) at rt overnight. The mixture was filtrated (celite) and concentrated in vacuo. To the residue, AcOEt and hexanes were added and the crystal was collected by filtration to give methyl 2-amino-4-[5-(5,6,7,8-tetrahydro-1,8-naphthyridin-2-yl)pentanoylamino]butanoate (1.90 g). MS m/z: 449 [M+H]$^+$.

To a solution of methyl 2-amino-4-[5-(5,6,7,8-tetrahydro-1,8-naphthyridin-2-yl)pentanoylamino]butanoate (50.00 mg, 143.50 umol) in THF (2.00 mL) was added 4-methyl-benzenesulfonyl chloride (30.09 mg, 157.85 umol) on ice bath. The mixture was stirred at rt overnight. The reaction was quenched with satd. NaHCO$_3$ and the mixture was extracted with AcOEt. The organic layer was washed with brine, dried over Na$_2$SO$_4$ and concentrated in vacuo. To the residue, MeOH (2 mL), THF (2 mL) and 1 M aq. NaOH (2 mL) were added and the mixture was stirred at rt overnight. The mixture was neutralized with 1 M HCl and the mixture was concentrated in vacuo. To the residue, MeOH and CH$_2$Cl$_2$ were added and the mixture was filtrated. The filtrate was purified by column chromatography on silica gel (0-40% MeOH in CH$_2$Cl$_2$). The residue was washed with MeOH/AcOEt/Hex to give 2-(p-tolylsulfonylamino)-4-[5-(5,6,7,8-tetrahydro-1,8-naphthyridin-2-yl)pentanoylamino] butanoic acid (14.00 mg, 28.65 umol, 19.97% yield). MS m/z: 489 [M+H]$^+$.

To 2-(p-tolylsulfonylamino)-4-[5-(5,6,7,8-tetrahydro-1,8-naphthyridin-2-yl)pentanoylamino]butanoic acid (9.50 mg, 19.44 umol) was added 1 M HCl aq. (19.44 umol, 1.00 mL). The solution was filtrated and concentrated in vacuo to give 2-(p-tolylsulfonylamino)-4-[5-(5,6,7,8-tetrahydro-1,8-naphthyridin-2-yl)pentanoylamino]butanoic acid hydrochloride (9.50 mg, 18.09 umol, 93.07% yield) as pale yellow solid. MS m/z: 489 [M+H]+.

GENERAL PROCEDURE FOR THE SYNTHESES OF EXAMPLES 15-37 AND 39-59

Methyl 2-amino-4-[5-(5,6,7,8-tetrahydro-1,8-naphthyridin-2-yl)pentanoylamino]butanoate was reacted with the appropriate acylating agent (carboxylic acid or carboxylic acid chloride for amides; chloroformate for carbamates; sulfonyl chloride for sulfonamides; or isocyanate for ureas) to produce the corresponding methyl butanoate. The methyl butanoate was saponified with 1 M aqueous sodium hydroxide in methanol/THF to produce the butanoic acids 15-37 and 39-59, shown in Table I below.

PROCEDURE FOR THE SYNTHESES OF EXAMPLES 38 AND 60-68

2-(Isobutoxycarbonylamino)-4-[5-(5,6,7,8-tetrahydro-1,8-naphthyridin-2-yl)pentanoylamino]butanoic acid Example 38

To a mixture of methyl 2-amino-4-[5-(5,6,7,8-tetrahydro-1,8-naphthyridin-2-yl)pentanoylamino]butanoate (300.00 mg, 860.98 umol) and NaHCO$_3$ (361.65 mg, 4.30 mmol) in THF (8.00 mL) and water (2.00 mL) was added isobutyl carbonochloridate (235.19 mg, 1.72 mmol, 223.35 uL) at rt. The mixture was stirred at rt for 2 days. The reaction was quenched with water and extracted with AcOEt. The organic layer was washed with water and brine, dried over Na$_2$SO$_4$ and concentarated in vacuo. The residue was purified by column chromatography (NH, 50-100% AcOEt in Hex) to give methyl 2-(isobutoxycarbonylamino)-4-[5-(5,6,7,8-tetrahydro-1,8-naphthyridin-2-yl)pentanoylamino]butanoate (332.00 mg, 740.16 umol, 85.97% yield) as colorless oil.

To a mixture of methyl 2-(isobutoxycarbonylamino)-4-[5-(5,6,7,8-tetrahydro-1,8-naphthyridin-2-yl)pentanoylamino]butanoate (332.00 mg, 740.16 umol), H$_2$O (1.00 mL), and THF (4.00 mL) was added lithium hydroxide monohydrate (93.17 mg, 2.22 mmol) at room temperature. After being sitrred for 4 h, 1N HCl (1.0 M, 2.22 mL) was added to the reaction mixture. The mixture was concentrated in vacuo. The residue was purified by column chromatography (SI, 0-50% MeOH in CH$_2$Cl$_2$). The residue was washed with AcOEt to give 2-(isobutoxycarbonylamino)-4-[5-(5,6,7,8-tetrahydro-1,8-naphthyridin-2-yl)pentanoylamino]butanoic acid Example 38 (278.00 mg, 639.77 umol, 86.44% yield) as white solid. MS m/z: 435 [M+H]−.

In similar fashion, methyl 2-amino-4-[5-(5,6,7,8-tetrahydro-1,8-naphthyridin-2-yl)pentanoylamino]butanoate was reacted with the appropriate acylating agent (carboxylic acid or carboxylic acid chloride for amides; chloroformate for carbamates) to produce the corresponding methyl butanoate. The methyl butanoate was saponified with 1 M aqueous lithium hydroxide in methanol/THF or THF to produce the butanoic acids 60-68, shown in Table I below.

Procedure for the syntheses of Examples 69 and 70: To a solution of methyl 2-amino-4-[5-(5,6,7,8-tetrahydro-1,8-naphthyridin-2-yl)pentanoylamino]butanoate (101.20 mg, 290.44 umol) and triethylamine (58.78 mg, 580.88 umol, 80.52 uL) in THF (6.00 mL) was added 2-chlorobenzoxazole (89.21 mg, 580.88 umol, 66.32 uL) at room temperature. The mixture was stirred at room temperature for 1 hour, then warmed to 60° C. and stirred overnight. The mixture was then stirred at 80° C. for 2 days. The reaction mixture was filtered and concentrated in vacuo. The residue was purified by NH silica gel (hexane:EtOAc=80:20 to 0:100) to give methyl 2-(1,3-benzoxazol-2-ylamino)-4-[5-(5,6,7,8-tetrahydro-1,8-naphthyridin-2-yl)pentanoylamino]butanoate (62.40 mg, 134.04 umol, 46.15% yield) as a colorless oil. To a solution of methyl 2-(1,3-benzoxazol-2-ylamino)-4-[5-(5,6,7,8-tetrahydro-1,8-naphthyridin-2-yl)pentanoylamino] butanoate (62.40 mg, 134.04 umol) in THF (4.00 mL) and water (1.00 mL) was added LiOH(H$_2$O) (16.87 mg, 402.12 umol) at 0° C. The mixture was stirred at room temperature for 4 days. The reaction mixture was quenched with 1N HCl at 0° C. and concentrated in vacuo. The residue was purified by TLC plate (EtOAc:MeOH=1:1) and The silica gel was extracted with MeOH and concentrated in vacuo to give 2-(1,3-benzoxazol-2-ylamino)-4-[5-(5,6,7,8-tetrahydro-1,8-naphthyridin-2-yl)pentanoylamino]butanoic acid Example 69 (57.10 mg, 126.46 umol, 94.35% yield) as an amorphous solid. 1H NMR (500 MHz, Methanol-d4) δ 7.22-7.12 (m, 2H), 7.11-7.02 (m, 2H), 6.94 (dd, J=7.8, 1.3 Hz, 1H), 6.29 (d, J=7.3 Hz, 1H), 4.18 (dd, J=7.8, 4.7 Hz, 1H), 3.29 (dd, J=4.7, 2.9 Hz, 2H), 3.24 (m, 7H), 2.61 (t, J=6.4 Hz, 2H), 2.46 (d, J=7.1 Hz, 2H), 2.18-2.06 (m, 3H), 1.95-1.88 (m, 1H), 1.80-1.73 (m, 2H), 1.56 (dt, J=7.1, 3.6 Hz, 4H).

2-(1,3-Benzothiazol-2-ylamino)-4-[5-(5,6,7,8-tetrahydro-1,8-naphthyridin-2-yl)pentanoylamino]butanoic acid Example 70 was prepared in similar fashion using 2-fluorobenzothiazole in place of 2-chlorobenzoxazole.

Examples 71-73, 2-[(6-methoxypyridine-2-carbonyl)amino]-4-[5-(5,6,7,8-tetrahydro-1,8-naphthyridin-2-yl)pentanoylamino]butanoic acid Example 71; 2-[(5-phenylthiazole-2-carbonyl)amino]-4-[5-(5,6,7,8-tetrahydro-1,8-naphthyridin-2-yl)pentanoylamino]butanoic acid Example 72; and 2-[[1-(cyclopropylmethyl)benzimidazole-2-carbonyl]amino]-4-[5-(5,6,7,8-tetrahydro-1,8-naphthyridin-2-yl)pentanoylamino]butanoic acid Example 73 were prepared as described above using methyl 2-amino-4-[5-(5,6,7,8-tetrahydro-1,8-naphthyridin-2-yl)pentanoylamino]butanoate, HOBt, trimethylamine, 3-(ethyliminomethyleneamino)-N,N-dimethyl-propan-1-amine hydrochloride and the appropriate carboxylic acid. The methyl ester was saponified with lithium hydroxide as described for Examples 69 and 70.

The starting material for Example 73, ethyl 1-(cyclopropylmethyl)benzimidazole-2-carboxylate, was prepared by stirring a mixture of ethyl 1H-benzimidazole-2-carboxylate (1.00 g, 5.26 mmol), iodomethylcyclopropane (1.44 g, 7.89 mmol, 736.07 µL) and K$_2$CO$_3$ (3.63 g, 26.29 mmol) in DMF (5.00 mL) at rt overnight. The reaction was quenched with water and extracted with AcOEt, washed with brine, dried over Na$_2$SO$_4$ and concentrated in vacuo. The residue was purified by column chromatography (SI, 20-50% AoOEt in Hex) to give ethyl 1-(cyclopropylmethyl)benzimidazole-2-carboxylate (1.18 g, 4.83 mmol, 91.83% yield) as white solid. To a mixture of ethyl 1-(cyclopropylmethyl)benzimidazole-2-carboxylate (300.00 mg, 1.23 mmol), H$_2$O (1.00 mL), and THF (4.00 mL) was added lithium hydroxide monohydrate (154.59 mg, 3.68 mmol) at room temperature. After being stirred at rt for 3 h, 1N HCl (1.0 M, 2.46 mL) was added to the reaction mixture and the mixture was concentrated in vacuo to give 1-(cyclopropylmethyl)benzimidazole-2-carboxylic acid mixture. This product was used without purification.

Procedure for the syntheses of Examples 74 and 75: To a mixture of methyl 2-amino-4-[5-(5,6,7,8-tetrahydro-1,8-naphthyridin-2-yl)pentanoylamino]-butanoate (100.00 mg, 286.99 µmol), H$_2$O (500.00 µL), and THF (2.00 mL) was added lithium hydroxide monohydrate (36.13 mg, 860.98

µmol) at room temperature. After being sitrred at rt overnight, 1N HCl (1.0 M, 860.98 uL) was added to the reaction mixture. The mixture was concentrated in vacuo to give 2-amino-4-[5-(5,6,7,8-tetrahydro-1,8-naphthyridin-2-yl) pentanoylamino]butanoic acid as white solid. This product was used in the next reaction without purification. To a solution of 1,3-benzoxazole-2-carboxylic acid (55.99 mg, 343.20 umol) in CH$_2$Cl$_2$ (4.00 mL) was added oxalyl chloride (58.08 mg, 457.60 µmol, 38.72 uL) and DMF (2.09 mg, 28.60 µmol, 2.22 uL) on ice bath. The mixture was stirred at rt for 3 h. The mixture was concentrated in vacuo and the residue was dissolved in dioxane (2.00 mL) to give acid chloride solution. 2-Amino-4-[5-(5,6,7,8-tetrahydro-1,8-naphthyridin-2-yl)pentanoylamino]butanoic acid (95.64 mg, 286.00 µmol) and sodium carbonate (151.57 mg, 1.43 mmol) were dissolved in water (2.00 mL) and acidchloride solution was added dropwise on ice bath. The mixture was stirred at rt overnight. The mixture was concentrated in vacuo. The residue was purified by column chromatography (SI, 0-50% MeOH in CH$_2$Cl$_2$) and the product was washed with MeOH/AcOEt to give 2-(1,3-benzoxazole-2-carbonylamino)-4-[5-(5,6,7,8-tetrahydro-1,8-naphthyridin-2-yl) pentanoylamino]butanoic acid Example 74 (12.00 mg, 25.02 µmol, 8.75% yield) as white solid.

For Example 75 an acid chloride solution was prepared by: To a suspension of 1,3-benzothiazole-2-carboxylic acid (394.24 mg, 2.20 mmol) in CH$_2$Cl$_2$ (10.00 mL) was added (COCl)$_2$ (418.87 mg, 3.30 mmol, 279.25 µL) and one drop of DMF on ice bath. The mixture was stirred at rt for 3 h. The mixture was concentrated in vacuo. To the residue, 5 mL of DMF was added to give acid chloride solution.

To a mixture of 2-amino-4-[5-(5,6,7,8-tetrahydro-1,8-naphthyridin-2-yl)pentanoylamino]butanoic acid (407.96 mg) in DMF (10.00 mL) were added acid chloride solution and TEA (222.62 mg, 2.20 mmol, 304.96 uL) at rt. The mixture was stirred at rt for 2 h. The reaction was quenched with water and satd.NaHCO$_3$ and the mixture was concentrated in vacuo. To the residue, MeOH and CH$_2$Cl$_2$ were added and filtered. The filtrate was concentrated in vacuo. The residue was purified by column chromatography (SI, 0-50% MeOH in CH$_2$Cl$_2$) and crystallized from MeOH/AcOEt to give 2-(1,3-benzothiazole-2-carbonylamino)-4-[5-(5,6,7,8-tetrahydro-1,8-naphthyridin-2-yl)pentanoylamino]butanoic acid Example 75 (74.60 mg, 150.53 umol, 13.68% yield) as white solid. NMR $^1$H NMR (500 MHz, DMSO-d$_6$) δ 9.16 (d, J=7.7 Hz, 1H), 8.26 (d, J=8.0 Hz, 1H), 8.19 (d, J=8.0 Hz, 1H), 7.88 (t, J=5.5 Hz, 1H), 7.70-7.58 (m, 2H), 7.11 (d, J=7.2 Hz, 1H), 6.95 (brs, 1H), 6.30 (d, J=7.2 Hz, 1H), 4.45-4.37 (m, 1H), 3.27 (t, J=5.6 Hz, 2H), 3.24-3.08 (m, 2H), 2.62 (t, J=6.3 Hz, 2H), 2.45 (t, J=7.4 Hz, 2H), 2.13-1.97 (m, 4H), 1.81-1.72 (m, 2H), 1.60-1.45 (m, 4H).

Procedure for the syntheses of Examples 76 and 77: To a solution of methyl 4-(tert-butoxycarbonylamino)-2-hydroxy-butanoate (1.00 g, 4.29 mmol) in CH$_2$Cl$_2$ (50.00 mL) were added CBr$_4$ (1.71 g, 5.15 mmol) and PPh$_3$ (1.35 g, 5.15 mmol) on ice bath. The mixture was stirred at rt for 3 h. The reaction was quenched with water and extracted with AcOEt, washed with water and brine, dried over Na$_2$SO$_4$ and concentrated in vacuo. The residue was purified by column chromatography (SI, 10-30% AcOEt in Hexanes) to give methyl 2-bromo-4-(tert-butoxycarbonylamino)butanoate (747.00 mg, 2.52 mmol, 58.79% yield) as colorless oil. $^1$H NMR (500 MHz, DMSO-d$_6$) δ 6.94 (t, J=5.7 Hz, 1H), 4.55 (dd, J=8.3, 5.9 Hz, 1H), 3.72 (s, 3H), 3.15-2.96 (m, 2H), 2.22-2.09 (m, 1H), 2.05-1.90 (m, 1H), 1.39 (s, 9H).

To a solution of methyl 2-bromo-4-(tert-butoxycarbonylamino)butanoate (747.00 mg, 2.52 mmol) in DIVIF (5.00 mL) was added NaN$_3$ (327.95 mg, 5.04 mmol) at rt. The mixture was stirred at rt for 4 h. The reaction was quenched with water and extracted with AcOEt. The organic layer was washed with water and brine, dried over Na$_2$SO$_4$ and concentrated in vacuo. The residue was purified by column chromatography (SI, 10-50% AcOEt in Hexanes) to give methyl 2-azido-4-(tert-butoxycarbonylamino)butanoate (612.00 mg, 2.37 mmol, 94.03% yield) as a colorless oil. $^1$H NMR (500 MHz, DMSO-d$_6$) δ 6.94 (t, J=5.8 Hz, 1H), 4.30 (dd, J=9.4, 4.3 Hz, 1H), 3.74 (s, 3H), 3.12-2.95 (m, 2H), 1.97-1.83 (m, 1H), 1.77-1.63 (m, 1H), 1.39 (s, 9H).

A mixture of methyl 2-azido-4-(tert-butoxycarbonylamino)butanoate (300.00 mg, 1.16 mmol), ethynylbenzene (177.71 mg, 1.74 mmol, 191.08 uL), CuI (110.46 mg, 580.00 µmol) and TEA (234.76 mg, 2.32 mmol, 321.59 µL) in DMF (5.00 mL) was stirred at rt overnight. The reaction was quenched with water and the mixture was extracted with AcOEt. The organic layer was washed with water and brine, dried over Na$_2$SO$_4$ and concentrated in vacuo. The residue was purified by column chromatography (SI, 10-50% AcOEt in Hexanes) to give methyl 4-(tert-butoxycarbonylamino)-2-(4-phenyltriazol-1-yl)butanoate (280.00 mg, 675.90 umol, 58.27% yield, 87% purity) as colorless oil.

A mixture of 4-(tert-butoxycarbonylamino)-2-(4-phenyl-triazol-1-yl)butanoate (280.00 mg, 776.89 umol) and HCl (1 M in AcOEt) (776.89 µumol) was stirred at rt for 4 days. The solid was filtrated to give methyl 4-amino-2-(4-phenyltriazol-1-yl)butanoate (234.00 mg, 709.69 umol, 91.35% yield, 90% purity, CL) as white solid. MS m/z: 261 [M+H]$^-$.

To a mixture of 5-(5,6,7,8-tetrahydro-1,8-naphthyridin-2-yl)pentanoic acid (71.06 mg, 303.29 µmol), methyl 4-amino-2-(4-phenyltriazol-1-yl)butanoate (100.00 mg, 303.29 µmol, CL) and DIPEA (97.99 mg, 758.22 µmol, 132.42 uL) in DMF (2.00 mL) was added HATU (137.31 mg, 363.95 µmol) at rt. The mixture was stirred at rt overnight. The reaction was quenched with water and the mixture was extracted with AcOEt. The organic layer was washed with water and brine, dried over Na$_2$SO$_4$ and concentrated in vacu. The residue was purified by column chromatography (NH, 50-100% AcOEt in Hexanes; SI, 0-50% MeOH in AcOEt) to give methyl 2-(4-phenyltriazol-1-yl)-4-[5-(5,6,7,8-tetrahydro-1,8-naphthyridin-2-yl)pentanoylamino]butanoate (41.00 mg, 86.03 umol, 28.37% yield) as colorless oil. MS m/z: 477[M+H]$^+$.

To a mixture of methyl 2-(4-phenyltriazol-1-yl)-4-[5-(5,6,7,8-tetrahydro-1,8-naphthyridin-2-yl)pentanoylamino]butanoate (41.00 mg, 86.03 µmol), H$_2$O (500.00 and THF (2.00 mL) was added lithium hydroxide monohydrate (10.83 mg, 258.09 µmol) at room temperature. After being stirred at rt overnight, 1N HCl (1.0 M, 258.09 µL) was added to the reaction mixture. The mixture was concentrated in vacuo. The residue was washed with water and MeOH to give 2-(4-phenyltriazol-1-yl)-4-[5-(5,6,7,8-tetrahydro-1,8-naphthyridin-2-yl)pentanoylamino]butanoic acid Example 76 (28.00 mg, 60.54 µmol, 70.37% yield) as white solid. MS m/z: 463[M+H]$^+$.

Example 77, 2-(4-isobutyltriazol-1-yl)-4-[5-(5,6,7,8-tetrahydro-1,8-naphthyridin-2-yl)pentanoylamino]butanoic acid was made in analogous fashion to Example 76, using 4-methyl-1-pentyne in place of ethynylbenzene.

PROCEDURE FOR THE SYNTHESIS OF EXAMPLE 78

To a solution of methyl 4-(tert-butoxycarbonylamino)-2-hydroxy-butanoate (601.81 mg, 2.58 mmol) in THF (5.00 mL) were added PPh3 (676.71 mg, 2.58 mmol) and diisopropy azodicarboxylate (DIAD) (521.70 mg, 2.58 mmol, 507.98 uL) on ice bath. The mixture was stirred at rt for 3 h. The reaction was quenched with water and extracted with AcOEt, washed with water and brine, dried over Na$_2$SO$_4$ and concentrated in vacuo. The residue was purified by column chromatography (SI, 10-30% AcOEt in Hexanes) to give methyl 4-(tert-butoxycarbonylamino)-2-(3-phenyl-1,2,4-triazol-1-yl)butanoate (631.00 mg, 1.47 mmol, 85.50% yield, 84% purity) as a colorless oil. MS m/z: 361[M+H]$^+$.

A mixture of methyl 4-(tert-butoxycarbonylamino)-2-(3-phenyl-1,2,4-triazol-1-yl)butanoate (540.62 mg, 1.50 mmol) and HCl (1 M in AcOEt) (1 M, 8.71 mL) was stirred at rt overnight. The solid was filtrated and washed with AcOEt to give methyl 4-amino-2-(3-phenyl-1,2,4-triazol-1-yl)butanoate (445.00 mg, 1.50 mmol, 100.00% yield, CL) as white solid. MS m/z: 261[M+H]$^+$.

To a mixture of 5-(5,6,7,8-tetrahydro-1,8-naphthyridin-2-yl)pentanoic acid (157.90 mg, 673.97 umol), methyl 4-amino-2-(3-phenyl-1,2,4-triazol-1-yl)butanoate (200.00 mg, 673.97 μmol, CL) and DIPEA (261.31 mg, 2.02 mmol, 353.12 μL) in DMF (5.00 mL) was added HATU (305.12 mg, 808.76 μmol) at rt. The mixture was stirred at rt overnight. The reaction was quenched with water and the mixture was extracted with AcOEt. The organic layer was washed with water and brine, dried over Na$_2$SO$_4$ and concentrated in vacuo. The residue was purified by column chromatography (NH, 50-100% AcOEt in Hexanes) to give methyl 2-(3-phenyl-1,2,4-triazol-1-yl)-4-[5-(5,6,7,8-tetrahydro-1,8-naphthyridin-2-yl)pentanoylamino]butanoate (110.00 mg, 230.82 μmol, 34.25% yield) as colorless oil. MS m/z: 477[M+H]$^+$.

To a mixture of methyl 2-(3-phenyl-1,2,4-triazol-1-yl)-4-[5-(5,6,7,8-tetrahydro-1,8-naphthyridin-2-yl)pentanoylamino]butanoate (110.00 mg, 230.82 umol), H$_2$O (500.00 μL), and THF (2.00 mL) was added lithium hydroxide monohydrate (29.06 mg, 692.45 μmol) at room temperature. After being stirred at rt for 5 h, 1N HCl (1.0 M, 692.45 uL) was added to the reaction mixture. The mixture was concentrated in vacuo. The residue was purified by column chromatography (SI, 0-20% MeOH in CH$_2$Cl$_2$). The reside was washed with AcOEt to give 2-(3-phenyl-1,2,4-triazol-1-yl)-4-[5-(5,6,7,8-tetrahydro-1,8-naphthyridin-2-yl)pentanoylamino]butanoic acid Example 78 (76.00 mg, 164.31 umol, 71.19% yield) as white solid. $^1$H NMR (500 MHz, DMSO-d$_6$) δ 8.65 (s, 1H), 8.05-7.98 (m, 3H), 7.55-7.39 (m, 4H), 7.19 (d, J=7.2 Hz, 1H), 6.35 (d, J=7.2 Hz, 1H), 5.16 (dd, J=9.2, 4.9 Hz, 1H), 3.30-3.16 (m, 2H), 3.15-2.94 (m, 2H), 2.64 (t, J=6.3 Hz, 2H), 2.52-2.24 (m, 4H), 2.10 (t, J=6.8 Hz, 2H), 1.81-1.71 (m, 2H), 1.63-1.48 (m, 4H). MS m/z: 463[M+H]$^+$.

PROCEDURE FOR THE SYNTHESIS OF EXAMPLE 79

To a mixture of 5-bromo-2-methoxy-pyridine (8.00 g, 42.55 mmol), 4-ditert-butylphosphanyl-N,N-dimethyl-aniline;palladium(2+) dichloride (3.01 g, 4.26 mmol), and THF (150.00 mL) was added tert-butyl acetate chlorozinc(1+) in Et$_2$O (0.5 M, 100.37 mL) at room temperature. Then, the reaction mixture was heated to 60° C. After being stirred overnight, sat. NH$_4$Cl(aq) was added to the reaction mixture. After removal of organic solvents by evaporation, the extraction was carried out with EtOAc. The extract was washed with brine, dried over MgSO$_4$, and concentrated in vacuo. The residue was purified by column chromatography on NH silica (0-20% EtOAc/hexane) to give a yellow oil. The obtained oil was purified by column chromatography on silica (0-20% EtOAc/hexane) to give tert-butyl 2-(6-methoxy-3-pyridyl)acetate (5.86 g, 26.25 mmol, 61.68% yield) as a pale yellow oil. $^1$H NMR (500 MHz, DMSO-d$_6$) δ 8.03 (dd, J=2.5, 0.8 Hz, 1H), 7.60 (dd, J=8.5, 2.5 Hz, 1H), 6.80 (dd, J=8.5, 0.7 Hz, 1H), 3.84 (s, 3H), 3.53 (s, 2H), 1.41 (s, 9H).

A solution of tert-butyl 2-(6-methoxy-3-pyridyl)acetate (5.07 g, 22.72 mmol) in THF (50.00 mL) was added to lithium bis(trimethylsilyl)azanide THF solution (1.0 M, 24.99 mL) at −78° C. dropwise. After being stirred for 2 h at that temperature, a solution of bromoacetonitrile (5.45 g, 45.44 mmol, 3.16 mL) in THF (10 ml) was added to the reaction mixture. Then, the reaction mixture was warmed to room temperature slowly. After being stirred overnight, sat.NH$_4$Cl(aq) was added to the reaction mixture. The extraction was carried out with EtOAc. The extract was washed with brine, dried over MgSO$_4$, and concentrated in vacuo. A solution of the residue in THF (25 ml) was added to lithium bis(trimethylsilyl)azanide THF solution (1.0 M, 24.99 mL) at 0° C. After being stirred for 1.5 h, a solution of bromoacetonitrile (5.45 g, 45.44 mmol, 3.16 mL) in THF (5 ml) was added to the mixture at that temperature. After being stirred overnight, sodium hydride (60% in oil) (1.36 g, 34.08 mmol, 60% purity) was added to the reaction mixture at 0° C. After being stirred for 5 h at that temperature, sat.NH$_4$Cl(aq) was added to the reaction mixture. The extraction was carried out with EtOAc. The extract was washed with brine, dried over MgSO$_4$, and concentrated in vacuo. The residue was purified by column chromatography on silica (0-30% EtOAc/hexane) to give tert-butyl 3-cyano-2-(6-methoxy-3-pyridyl)propanoate (980.00 mg, 3.74 mmol, 16.44% yield) as a pale yellow oil $^1$H NMR (500 MHz, DMSO-d$_6$) δ 8.12 (d, J=2.5 Hz, 1H), 7.66 (dd, J=8.6, 2.6 Hz, 1H), 6.85 (d, J=8.7 Hz, 1H), 4.02 (t, J=7.4 Hz, 1H), 3.85 (s, 3H), 3.08 (dd, J=16.9, 7.2 Hz, 1H), 3.00 (dd, J=16.9, 7.5 Hz, 1H), 1.37 (s, 9H).

A solution of tert-butyl 3-cyano-2-(6-methoxy-3-pyridyl)propanoate (980.00 mg, 3.74 mmol) in MeOH (20.00 mL) and AcOH (5.00 mL) was hydrogenated by H-Cube (Rany Ni) under 50 bar at 50° C. After being flowed through the cartridge (1.0 ml/min) overnight, the mixture was concentrated in vacuo. To a solution of the residue in MeOH (20 ml) was added PtO$_2$ (300.00 mg, 3.74 mmol). The mixture was stirred at 50° C. under H$_2$. After being stirred for 3 h, PtO$_2$ was removed by filtration and washed with EtOAc. The filtrate was concentrated in vacuo. The residue was purified by NH silica gel column chromatography (0%-100% EtOAc in hexane) to give tert-butyl 4-amino-2-(6-methoxy-3-pyridyl)butanoate (127.10 mg, 477.21 umol, 12.77% yield) as a white solid. MS m/z: 267[M+H]$^+$.

To a mixture of 5-(5,6,7,8-tetrahydro-1,8-naphthyridin-2-yl)pentanoic acid (134.17 mg, 572.65 umol), HATU (216.04 mg, 572.65 umol), and DMF (4.00 mL) was added DIPEA (215.86 mg, 1.67 mmol, 291.70 μL) at room temperature. After being stirred for 2 h, a solution of tert-butyl 4-amino-2-(6-methoxy-3-pyridyl)butanoate (127.10 mg, 477.21 μmol) in DMF (4 mL) was added to the reaction mixture. After being stirred overnight, water was added to the reaction mixture. The extraction was carried out with EtOAc. The extract was washed with brine, dried over MgSO$_4$, and concentrated in vacuo. The residue was purified by column chromatography on NH silica (20-100% EtOAc/hexane) to give tert-butyl 2-(6-methoxy-3-pyridyl)-4-[5-(5,6,7,8-tetrahydro-1,8-naphthyridin-2-yl)pentanoylamino]butanoate as a colorless oil. MS m/z: 483 [M+H]$^+$.

To a solution of tert-butyl 2-(6-methoxy-3-pyridyl)-4-[5-(5,6,7,8-tetrahydro-1,8-naphthyridin-2-yl)pentanoylamino]

butanoate (230.31 mg, 477.21 umol) in CH$_2$Cl$_2$ (2.00 mL) was added TFA (54.41 mg, 477.21 umol, 1.00 mL) at room temperature. After being stirred for 1 h, the reaction mixture was concentrated in vacuo. The residue was purified by column chromatography on NH silica (0-100% MeOH/EtOAc) to give a colorless oil. The obtained oil was purified by column chromatography on silica (0-20% MeOH/EtOAc) to give a white solid. The obtained solid was washed with 50% EtOAc/hexane to give 2-(6-methoxy-3-pyridyl)-4-[5-(5,6,7,8-tetrahydro-1,8-naphthyridin-2-yl)pentanoylamino]butanoic acid Example 79 (47.60 mg, 111.60 umol, 23.39% yield) as a white solid. MS m/z: 427[M+H]$^+$.

PROCEDURE FOR THE SYNTHESIS OF EXAMPLE 80

To a mixture of 5-bromo-2-phenoxy-pyridine (9.75 g, 38.99 mmol), 4-ditert-butylphosphanyl-N,N-dimethyl-aniline palladium(2+);dichloride (2.76 g, 3.90 mmol), and THF (250.00 mL) was added tert-butyl acetate chlorozinc(1+) in Et$_2$O (0.5 M, 93.58 mL) at room temperature. Then, the reaction mixture was heated to 60° C. After being stirred overnight, sat. NH$_4$Cl(aq) was added to the reaction mixture. The mixture was extracted with AcOEt, washed with brine, dried over Na$_2$SO$_4$ and concentrated in vacuo. The residue was purified by column chromatography (NH, 0-20% AcOEt in hexanes; SI, 0-20% AcOEt in hexanes) to give tert-butyl 2-(6-phenoxy-3-pyridyl)acetate (7.57 g, 26.53 mmol, 68.04% yield) as pale yellow oil. MS m/z: 286 [M+H]$^+$.

To a solution of tert-butyl 2-(6-phenoxy-3-pyridyl)acetate (7.00 g, 24.53 mmol) in THF (100.00 mL) was added lithium bis(trimethylsilyl)azanide (1.0 M, 24.53 mL) on ice bath. The mixture was stirred on ice bath for 10 min. To the mixture, bromoacetonitrile (2.94 g, 24.53 mmol, 1.71 mL) was added dropwise on ice bath and the mixture was stirred on ice bath for 1 h. To the mixture lithium bis(trimethylsilyl)azanide (1.0 M, 24.53 mL) was added on ice bath and the mixture was stirred on ice bath for 10 min. The reaction was not complete, so a further portion of bromoacetonitrile (5.88 g, 49.06 mmol, 3.42 mL) was added dropwise on ice bath. The mixture was stirred on ice bath for 1 h. The reaction was quenched with satd. NH$_4$Cl and extracted with AcOEt. The organic layer was washed with brine, dried over Na$_2$SO$_4$ and concentrated in vacuo. The residue was purified by column chromatography (SI, 0-50% AcOET in Hexanes) to give tert-butyl 3-cyano-2-(6-phenoxy-3-pyridyl)propanoate (1.45 g, 4.47 mmol, 18.22% yield) as colorless oil. MS m/z: 325[M+H]$^+$.

To a solution of the residue in MeOH (20.00 mL) was added PtO$_2$ (300.00 mg, 4.47 mmol). The mixture was stirred at rt under H$_2$ overnight. PtO$_2$ was removed by filtration and washed with EtOAc. The filtrate was concentrated in vacuo. The residue was purified by NH silica gel column chromatography (0%-100% EtOAc in hexane) to give tert-butyl 4-amino-2-(6-phenoxy-3-pyridyl)butanoate (200.00 mg, 609.01 umol, 13.62% yield) as colorless oil. MS m/z: 329[M+H]$^+$.

To a solution of 5-(5,6,7,8-tetrahydro-1,8-naphthyridin-2-yl)pentanoic acid (171.22 mg, 730.81 umol), tert-butyl 4-amino-2-(6-phenoxy-3-pyridyl)butanoate (200.00 mg, 609.01 umol) in DMF (3.00 mL) were added HATU (275.71 mg, 730.81 umol) and DIPEA (94.45 mg, 730.81 umol, 127.64 uL) at rt. The mixture was stirred at rt overnight. The reaction was quenched with water and extracted with AcOEt. The organic layer was washed with water and brine, dried over Na$_2$SO$_4$ and concentrated in vacuo. The residue was purified by column chromatography (NH, 50-100% AcOEt in Hexanes) to give tert-butyl 2-(6-phenoxy-3-pyridyl)-4-[5-(5,6,7,8-tetrahydro-1,8-naphthyridin-2-yl)pentanoylamino]butanoate (166.00 mg, 304.77 umol, 50.04% yield) as colorless oil. $^1$H NMR (500 MHz, DMSO-d$_6$) δ 8.06-7.98 (m, 1H), 7.83-7.71 (m, 2H), 7.51-7.39 (m, 2H), 7.23 (t, J=7.4 Hz, 1H), 7.14 (d, J=7.8 Hz, 2H), 7.04-6.93 (m, 2H), 6.27-6.15 (m, 2H), 3.57 (t, J=7.5 Hz, 1H), 3.26-3.19 (m, 2H), 3.04-2.87 (m, 2H), 2.60 (t, J=6.2 Hz, 2H), 2.42 (t, J=7.3 Hz, 2H), 2.12-1.98 (m, 3H), 1.82-1.72 (m, 3H), 1.59-1.41 (m, 4H), 1.37 (s, 9H).

To a solution of tert-butyl 2-(6-phenoxy-3-pyridyl)-4-[5-(5,6,7,8-tetrahydro-1,8-naphthyridin-2-yl)pentanoylamino]butanoate (166.00 mg, 304.77 umol) in CH$_2$Cl$_2$ (2.00 mL) was added TFA (34.75 mg, 304.77 umol, 1.00 mL) at rt. The mixture was stirred at rt for 3 h. The mixture was concentrated in vacuo. The residue was purified by column chromatograpy (SI, 0-30% MeOH in CH$_2$Cl$_2$). To the residue, CH$_2$Cl$_2$ and 2 M HCl in Et$_2$O (0.5 ml) were added and the mixture was concentrated in vacuo. The reside was washed with AcOEt to give 2-(6-phenoxy-3-pyridyl)-4-[5-(5,6,7,8-tetrahydro-1,8-naphthyridin-2-yl)pentanoylamino]butanoic acid Example 80 (111.00 mg, 211.41 μmol, 69.37% yield, CL) as pale yellow solid. MS m/z: 489[M+H]$^+$.

PROCEDURE FOR THE SYNTHESIS OF EXAMPLE 81

To a solution of methyl 2-amino-4-[5-(5,6,7,8-tetrahydro-1,8-naphthyridin-2-yl)pentanoylamino]butanoate (300.00 mg, 860.98 umol), 5-bromo-2-chloropyrimidine (199.85 mg, 1.03 mmol), DIEA (222.55 mg, 1.72 mmol, 300.74 uL), and tert-BuOH (6.00 mL) was heated to 100° C. After being stirred three days, the reaction mixture was concentrated in vacuo. The residue was purified by column chromatography on NH silica (30-100% EtOAc/hexane, then 0-10% MeOH/EtOAc) to give methyl 2-[(5-bromopyrimidin-2-yl)amino]-4-[5-(5,6,7,8-tetrahydro-1,8-naphthyridin-2-yl)pentanoylamino]butanoate (199.70 mg, 395.12 umol, 45.89% yield) as a colorless oil. MS m/z: 506, 508[M+H]$^+$.

A mixture of methyl 2-[(5-bromopyrimidin-2-yl)amino]-4-[5-(5,6,7,8-tetrahydro-1,8-naphthyridin-2-yl)pentanoylamino]butanoate (199.70 mg, 395.12 umol), phenyboronic acid (72.27 mg, 592.68 umol), sodium carbonate (125.64 mg, 1.19 mmol), palladium triphenylphosphane (45.66 mg, 39.51 umol), and DME (5.00 mL) was heated to 150° C. under the microwave irradiation. After being stirred for 1 h, the insoluble materials were removed by filtration and washed with EtOAc. The filtrate was concentrated in vacuo. The residue was purified by column chromatography on NH silica (0-100% EtOAc/hexane, then 0-20% MeOH in EtOAc) to give methyl 2-[(5-phenylpyrimidin-2-yl)amino]-4-[5-(5,6,7,8-tetrahydro-1,8-naphthyridin-2-yl)pentanoylamino]butanoate (74.50 mg, 148.23 umol, 37.51% yield) as a colorless oil. MS m/z: 503[M+H]$^+$.

To a mixture of methyl 2-[(5-phenylpyrimidin-2-yl)amino]-4-[5-(5,6,7,8-tetrahydro-1,8-naphthyridin-2-yl)pentanoylamino]butanoate (74.50 mg, 148.23 umol), THF (3.00 mL), MeOH (3.00 mL), and H$_2$O (1.00 mL) was added lithium hydroxide monohydrate (12.44 mg, 296.46 umol). After being stirred overnight, 1N HCl (1.0 M, 296.46 μL) was added to the reaction mixture. Then, the reaction mixture was concentrated in vacuo. The residue was purified by column chromatography on silica (0-50% MeOH in EtOAc) to give a colorless oil. The obtained oil was precipitated from 50% EtOAc/hexane to give 2-[(5-phenylpyrimidin-2-yl)amino]-4-[5-(5,6,7,8-tetrahydro-1,8-naphthyridin-2-yl)pentanoylamino]butanoic acid Example 81 (15.60 mg, 31.93 umol, 21.54% yield) as an off-white solid. MS m/z: 489[M+H]+.

PROCEDURE FOR THE SYNTHESIS OF EXAMPLE 82 AND EXAMPLE 83

To a solution of 5-(3-cyclopropyl-5,6,7,8-tetrahydro-1,8-naphthyridin-2-yl)pentanoic acid (488.36 mg, 1.78 mmol), methyl 4-amino-2-(benzyloxycarbonylamino)butanoate (710.99 mg, 2.67 mm), and HATU (1.01 g, 2.67 g) in DMF (20.00 mL) was added triethylamine (540.35 mg, 5.34 mmol, 740.21 uL). The reaction mixture was stirred at room temperature overnight. The organic layer was washed with brine (×2), dried over $Na_2SO_4$ and concentrated in vacuo. The residue was purified by NH silica gel (hexane:EtOAc=80:20 to 0:100) to give a mixture as a white solid. The solid compound was purified by NH silica gel (hexane:EtOAc=80:20 to 10:90) to give methyl 2-(benzyloxycarbonylamino)-4-[5-(3-cyclopropyl-5,6,7,8-tetrahydro-1,8-naphthyridin-2-yl)pentanoylamino]butanoate (928.00 mg, 1.78 mmol, 99.75% yield) as a mixture. The product was not purified further. MS m/z: 523 [M+H]+.

To a solution of methyl 2-(benzyloxycarbonylamino)-4-[5-(3-cyclopropyl-5,6,7,8-tetrahydro-1,8-naphthyridin-2-yl) pentanoylamino]butanoate (133.00 mg, 254.48 umol) in THF (4.00 mL) and water (1.00 mL) was added LiOH(H2O) (35.00 mg, 834.69 umol) at 0° C. The solution was stirred at room temperature overnight. The reaction mixture was concentrated in vacuo. The residue was purified by silica gel ($CH_2Cl_2$:MeOH=100:0 to 50:50) to give a mixture. The mixture was purified by silica gel ($CH_2Cl_2$:MeOH=100:0 to 80:20) to give a white solid. The solid was recrystalized from MeOH-hexane to give 2-(benzyloxycarbonyl-amino)-4-[5-(3-cyclopropyl-5,6,7,8-tetrahydro-1,8-naphthyridin-2-yl)pentanoyl-amino]butanoic acid, Example 82 (20.90 mg, 41.09 umol, 16.15% yield) as a white solid. MS m/z: 509[M+H]+.

To a solution of methyl 2-(benzyloxycarbonylamino)-4-[5-(3-cyclopropyl-5,6,7,8-tetrahydro-1,8-naphthyridin-2-yl) pentanoylamino]butanoate (790.00 mg, 1.51 mmol) in MeOH (35.00 mL) was added palladium on activated charcoal (10%) (79.00 mg) at room temperature under $N_2$. The mixture was stirred at room temperature under $H_2$ overnight. The reaction mixture was filtered and concentrated in vacuo. The residue was purified by NH-silica gel (EtOAc:MeOH=100:0 to 80:20) to give methyl 2-amino-4-[5-(3-cyclopropyl-5,6,7,8-tetrahydro-1,8-naphthyridin-2-yl)pentanoylamino]butanoate (384.90 mg, 990.73 umol, 65.61% yield) as a white solid. MS m/z: 389[M+H]+.

To a solution of methyl 2-amino-4-[5-(5,6,7,8-tetrahydro-1,8-naphthyridin-2-yl)pentanoylamino]butanoate (210.00 mg, 602.69 umol) and triethylamine (182.96 mg, 1.81 mmol, 250.63 uL) in THF (6.00 mL) was added 2-chlorobenzoxazole (185.11 mg, 1.21 mmol, 137.63 uL) at room temperature. The mixture was stirred at 80° C. overnight. The reaction mixture was quenched with sat. $NaHCO_3$ at 0° C. and diluted with EtOAc. The organic layer was separated, dried over $Na_2SO_4$ and concentrated in vacuo. The residue was purified by NH-silica gel (hexane:EtOAc=80:20 to 0:100) to give methyl 2-(1,3-benzoxazol-2-ylamino)-4-[5-(5,6,7,8-tetrahydro-1,8-naphthyridin-2-yl)pentanoylamino] butanoate as a pale yellow oil. The product was not purified further. MS m/z: 466[M+H]−.

To a solution of methyl 2-(1,3-benzoxazol-2-ylamino)-4-[5-(3-cyclopropyl-5,6,7,8-tetrahydro-1,8-naphthyridin-2-yl) pentanoylamino]butanoate (247.20 mg, 488.91 umol) in THF (5.00 mL) and Water (1.00 mL) was added LiOH(H2O) (72.60 mg, 1.73 mmol) at 0° C. The mixture was stirred at room temperature overnight. The reaction mixture was quenched with 1N HCl at 0° C., diluted with MeOH and concentrated in vacuo. The residue was purified by silica gel ($CH_2Cl_2$:MeOH=100:0 to 50:50) to give a mixture product. The mixture was purified by silica gel ($CH_2Cl_2$:MeOH=100:0 to 80:20) to give a mixture product. The residue was recrystallized from MeOH-EtOAc to give a white solid. The solid was recrystallized from MeOH to give 2-(1,3-benzoxazol-2-ylamino)-4-[5-(3-cyclopropyl-5,6,7,8-tetrahydro-1,8-naphthyridin-2-yl)pentanoylamino]butanoic acid, Example 83 (38.50 mg, 78.32 umol, 16.02% yield) as a white solid. MS m/z: 492[M+H]+.

The procedure for the synthesis of Example 84 was the same as for Example 79, using 3-bromoquinoline in place of 5-bromo-2-methoxypyridine to provide 2-(quinolin-3-yl)-4-(5-(5,6,7,8-tetrahydro-1,8-naphthyridin-2-yl)pentanamido) butanoic acid.

The procedure for the synthesis of Example 85 was the same as for Example 87 below, using methyl (2R)-2-(benzyloxycarbonylamino)-4-[5-(5,6,7,8-tetrahydro-1,8-naphthyridin-2-yl)pentanoylamino]butanoate (Example 6) in place of methyl (2S)-2-(benzyloxycarbonylamino)-4-[5-(5,6,7,8-tetrahydro-1,8-naphthyridin-2-yl)pentanoylamino]butanoate to provide (R)-2-(benzo[d]oxazol-2-ylamino)-4-(5-(5,6,7,8-tetrahydro-1,8-naphthyridin-2-yl)pentanamido) butanoic acid.

The procedure for the synthesis of Example 86 was the same as for Example 88 below, using methyl (2R)-2-(benzyloxycarbonylamino)-4-[5-(5,6,7,8-tetrahydro-1,8-naphthyridin-2-yl)pentanoylamino]butanoate (Example 6) in place of methyl (2S)-2-(benzyloxycarbonylamino)-4-[5-(5,6,7,8-tetrahydro-1,8-naphthyridin-2-yl)pentanoylamino]butanoate, to provide (R)-2-(benzo[d]thiazole-2-carboxamido)-4-(5-(5,6,7,8-tetrahydro-1,8-naphthyridin-2-yl) pentanamido)butanoic acid.

PROCEDURE FOR THE SYNTHESIS OF EXAMPLE 87

Methyl (2S)-2-(benzyloxycarbonylamino)-4-[5-(5,6,7,8-tetrahydro-1,8-naphthyridin-2-yl)pentanoylamino]butanoate (Example 2) (500.00 mg, 1.04 mmol) was dissolved in MeOH (5.00 mL). Pd(OH)2 (29.21 mg, 104.00 umol, 50% purity) was added and the mixture was stirred for 10 h under $H_2$ (15 psi) at rt. The reaction mixture was filtered and concentrated in vacuo to give methyl (2S)-2-amino-4-[5-(5,6,7,8-tetrahydro-1,8-naphthyridin-2-yl)pentanoylamino]butanoate (280.00 mg) as a colorless oil. The crude material was used in the next step without further purification.

To a solution of methyl (2S)-2-amino-4-[5-(5,6,7,8-tetrahydro-1,8-naphthyridin-2-yl)pentanoylamino]butanoate (280.00 mg, 803.58 umol) in DMF (3.00 mL) at 0° C. was added DIPEA (415.42 mg, 3.21 mmol, 561.38 uL, 4.00 eq), followed by 2-chloro-1,3-benzoxazole (148.09 mg, 964.30 umol, 109.70 uL, 1.20 eq). The reaction mixture was warmed to 25° C. and stirred for 20 h. The reaction mixture was quenched with water (15 mL) and extracted with EtOAc (15 mL*3), and the combined organic phase was washed with brine (5 mL), dried over $Na_2SO_4$ and concentrated in vacuo to give methyl (2S)-2-(1,3-benzoxazol-2-ylamino)-4-[5-(5,6,7,8-tetrahydro-1,8-naphthyridin-2-yl)pentanoylamino]butanoate (500.00 mg) as a yellow oil. The crude material was used in the next step without further purification. MS m/z: 466[M+H]−.

To a solution of methyl (2S)-2-(1,3-benzoxazol-2-ylamino)-4-[5-(5,6,7,8-tetrahydro-1,8-naphthyridin-2-yl)pentanoylamino]butanoate (480.00 mg, 1.03 mmol, 1.00 eq) in THF (5.00 mL) was added LiOH.H$_2$O (216.09 mg, 5.15 mmol, 5.00 eq) at 25° C., then the mixture was stirred at 25° C. for 2 h. The reaction mixture was quenched with water (10 mL) and then extracted three times with EtOAc (10 mL). The aqueous phase was acidified by 1N HCl to pH=7, and extracted five times with CH$_2$Cl$_2$/MeOH(10/1, 10 mL). The combined organic phase was washed with brine (5 mL), dried over Na$_2$SO$_4$ and concentrated in vacuo. The crude material was triturated in CH$_2$Cl$_2$ (3 mL) to give (2S)-2-(1,3-benzoxazol-2-ylamino)-4-[5-(5,6,7,8-tetrahydro-1,8-naphthyridin-2-yl)pentanoylamino]butanoic acid Example 87 (138.00 mg, 305.63 umol, 29.67% yield) as a white solid. MS m/z: 452[M+H]$^+$.

PROCEDURE FOR THE SYNTHESIS OF EXAMPLE 88

To a solution of methyl (2S)-2-amino-4-[5-(5,6,7,8-tetrahydro-1,8-naphthyridin-2-yl)pentanoylamino]butanoate (300.00 mg, 860.98 umol) and 1,3-benzothiazole-2-carboxylic acid (185.15 mg, 1.03 mmol) in DMF (4.00 mL) was added HATU (654.74 mg, 1.72 mmol) and DIPEA (333.82 mg, 2.58 mmol, 451.11 uL) at 25° C., and the mixture was stirred for 5 h. The reaction mixture was quenched with water (10 mL), then extracted three times with EtOAc (10 mL), and the combined organic phase was washed with brine (5 mL), dried over Na$_2$SO$_4$ and concentrated in vacuo. The crude was purified by column (CH$_2$Cl$_2$:MeOH=100:1 to 25:1) to give methyl (2S)-2-(1,3-benzothiazole-2-carbonylamino)-4-[5-(5,6,7,8-tetrahydro-1,8-naphthyridin-2-yl)pentanoylamino]butanoate (500.00 mg) as a yellow oil. MS m/z: 510[M+H]$^+$.

To a solution of methyl (2S)-2-(1,3-benzothiazole-2-carbonylamino)-4-[5-(5,6,7,8-tetrahydro-1,8-naphthyridin-2-yl)pentanoylamino]butanoate (500.00 mg, 981.12 umol, 1.00 eq) in THF (5.00 mL) and H$_2$O (1.00 mL) was added LiOH.H$_2$O (205.84 mg, 4.91 mmol, 5.00 eq) and the reaction mixture was stirred at 25° C. for 2 h, quenched with water (10 mL), and extracted with EtOAc (10 mL*3). The aqueous phase was acidified by 1N HCl to pH=7 and extracted with CH$_2$Cl$_2$/MeOH(10/1, 10 mL*5). The combined organic phase was washed with brine (5 mL), dried over Na$_2$SO$_4$ and concentrated in vacuo. The crude material was purified by prep-TLC(CH$_2$Cl$_2$:MeOH=10:1) to give (2S)-2-(1,3-benzothiazole-2-carbonylamino)-4-[5-(5,6,7,8-tetrahydro-1,8-naphthyridin-2-yl)pentanoylamino]butanoic acid Example 88 (94.00 mg, 189.67 umol, 19.33% yield) as a white solid. 1H NMR (400 MHz, CDCl3) δ 10.39 (1H, brs), 8.60 (1H, d, J=6.4 Hz), 8.13 (1H, d, J=8.4 Hz), 8.05 (1H, brs), 7.97 (1H, d, J=7.6 Hz), 7.55 (1H, t, J=7.6 Hz), 7.48 (1H, t, J=7.2 Hz), 7.28-7.29 (1H, m), 6.32 (1H, d, J=7.2 Hz), 4.48-4.52 (1H, m), 3.78-3.80 (1H, m), 3.52-3.55 (2H, m), 3.39-3.42 (1H, m), 2.80-2.85 (1H, m), 2.74-2.75 (2H, m), 2.50-2.53 (1H, m), 2.33-2.35 (2H, m), 2.16-2.18 (2H, m), 1.96-1.94 (m, 4H), 1.75-1.72 (m, 2H). 1H not found. MS m/z: 496[M+H]$^+$.

PROCEDURE FOR THE SYNTHESIS OF EXAMPLES 89-90

Propylphosphonic acid anhydride T3P (1.67 g, 2.63 mmol, 1.56 mL, 50% purity) was added to a solution of tert-butyl 4-amino-2-(3-quinolyl)butanoate (500.00 mg, 1.75 mmol), 5-(5,6,7,8-tetrahydro-1,8-naphthyridin-2-yl)pentanoic acid (492.01 mg, 2.10 mmol) 5-amino-2-(quinolin-3-yl)carboxylic acid t-butyl ester and DIPEA (452.34 mg, 3.50 mmol, 611.27 uL) in EtOAc (10.00 mL) at 0° C. The mixture was stirred for 2 h at 25° C. The residue was poured into water (20 mL) and the aqueous phase was extracted with ethyl acetate (10 mL*3). The combined organic phase was washed with brine (10 mL*3), dried with anhydrous Na$_2$SO$_4$, filtered and concentrated in vacuo. The residue was separated into two optical isomers (S or R) by silica gel chromatography (prep-HPLC (column: OD(250 mm*30 mm, 10 μm))) to give tert-butyl (S or R)-2-(3-quinolyl)-4-[5-(5,6,7,8-tetrahydro-1,8-naphthyridin-2-yl)pentanoylamino]butanoate (150.00 mg, 298.42 umol) (peak 1) as a yellow oil (MS m/z: 503 [M+H]$^+$) and tert-butyl (S or R)-2-(3-quinolyl)-4-[5-(5,6,7,8-tetrahydro-1,8-naphthyridin-2-yl)pentanoylamino]butanoate (150.00 mg, 298.42 umol) (peak 2) as a yellow oil.

TFA (68.05 mg, 596.84 umol, 44.19 uL) was added into the solution of tert-butyl (S or R)-2-(3-quinolyl)-4-[5-(5,6,7,8-tetrahydro-1,8-naphthyridin-2-yl)pentanoylamino]butanoate (100.00 mg, 198.95 umol) (peak 1) in CH$_2$Cl$_2$ (3.00 mL) at 25° C. The mixture was stirred for 2 h at 25° C. The mixture was concentrated in vacuo and the residue was poured into water (20 mL). The pH was adjusted to 7 by progressively adding sat. NaHCO$_3$. The aqueous phase was extracted with CH$_2$Cl$_2$ (15 mL*3). The combined organic phase was washed with brine (10 mL), dried with anhydrous Na$_2$SO$_4$, filtered and concentrated in vacuo to give 2-(3-quinolyl)-4-[5-(5,6,7,8-tetrahydro-1,8-naphthyridin-2-yl)pentanoylamino]butanoic acid (68.80 mg, 144.18 umol, 72.47% yield) as a yellow solid. MS m/z: 447[M+H]$^+$.

The procedure for the synthesis of Example 90 was the same as for Example 89.

The procedure for the synthesis of Example 91 (R)-2-((5-phenylpyrimidin-2-yl)amino)-4-(5-(5,6,7,8-tetrahydro-1,8-naphthyridin-2-yl)pentanamido)butanoic acid was the same as for Example 92, but starting with methyl (2R)-2-amino-4-(tert-butoxycarbonylamino)butanoate.

PROCEDURE FOR THE SYNTHESIS OF EXAMPLE 92

A solution of methyl (2S)-2-amino-4-(tert-butoxycarbonylamino)butanoate (590.00 mg, 2.20 mmol, HCl), 5-bromo-2-chloro-pyrimidine (425.55 mg, 2.20 mmol) and DIPEA (568.66 mg, 4.40 mmol, 768.46 uL) in t-BuOH (3.60 mL) was stirred for 48 h at 120° C. under N$_2$. The reaction was concentrated in vacuo and the residue was purified by column chromatography (SiO$_2$, PE/ETOAc=5/1 to 2:1) to give methyl (2S)-2-[(5-bromopyrimidin-2-yl)amino]-4-(tert-butoxycarbonylamino)butanoate (800.00 mg, 2.06 mmol, 93.42% yield) as a yellow oil. MS m/z: 388, 390 [M+H]$^+$.

Pd(dppf)Cl$_2$ (75.37 mg, 103.00 umol) was added to a solution of methyl (2S)-2-[(5-bromopyrimidin-2-yl)amino]-4-(tert-butoxycarbonylamino)butanoate (800.00 mg, 2.06 mmol), phenylboronic acid (301 mg, 2.47 mmol), and Na$_2$CO$_3$ (655.02 mg, 6.18 mmol) in dioxane (40.00 mL) and H$_2$O (8.00 mL). Then the mixture was degassed with N$_2$ 3 times. The mixture was heated to 90° C. for 12 h under N$_2$. The reaction was filtered and concentrated in vacuum. The residue was purified by column chromatography (SiO$_2$, PE/EtOAc=2/1 to 0/1) to give (2S)-4-(tert-butoxycarbonylamino)-2-[(5-phenylpyrimidin-2-yl)amino]butanoic acid (1.00 g, 1.13 mmol, 54.80% yield) as a yellow solid. MS m/z: 373 [M+H]$^+$.

To a solution of (2S)-4-(tert-butoxycarbonylamino)-2-[(5-phenylpyrimidin-2-yl)amino]butanoic acid (900.00 mg, 2.42 mmol) in MeOH (15.00 mL) was added TMSCHN$_2$ (2 M, 3.63 mL, 3.00 eq) at 0° C. and the reaction was stirred for 10 min at 0° C. The reaction was acidified with aqueous HCl (1 M) to pH=5 and extracted with EtOAc (40 mL*3). The combined organic phase was washed with brine (50 mL*2), dried with anhydrous Na$_2$SO$_4$, filtered and concentrated in vacuo. The residue was purified by column chromatography (SiO$_2$, PE/ETOAc=10/1 to 2:1) to give methyl (2S)-4-(tert-butoxycarbonylamino)-2-[(5-phenylpyrimidin-2-yl)amino]butanoate (540.00 mg, 1.15 mmol, 47.61% yield) as a yellow oil. MS m/z: 387 [M+H]$^+$.

To a solution of methyl (2S)-4-(tert-butoxycarbonylamino)-2-[(5-phenylpyrimidin-2-yl)amino]butanoate (600.00 mg, 1.55 mmol, 1.00 eq) in MeOH (2.00 mL) was added HCl/MeOH (4 M, 10.00 mL, 25.81 eq) at 25° C., and the reaction was stirred for 1 h at 25° C. The reaction was concentrated in vacuo to give methyl (2S)-4-amino-2-[(5-phenylpyrimidin-2-yl)amino]butanoate (600.00 mg, 1.53 mmol, 98.71% yield, 2HCl) as a yellow oil.

To a solution of 5-(5,6,7,8-tetrahydro-1,8-naphthyridin-2-yl)pentanoic acid (200.00 mg, 853.64 umol) in DMF (10.00 mL) was added HATU (486.87 mg, 1.28 mmol), DIPEA (441.30 mg, 3.41 mmol, 596.35 uL), and methyl (2S)-4-amino-2-[(5-phenylpyrimidin-2-yl)amino]butanoate (306.67 mg, 853.64 umol, 1.00 eq, 2HCl) at 0° C., and the reaction was stirred for 1 h at 0° C. The reaction was quenched with EtOAc (50 mL), washed with brine (30 mL*4), dried with anhydrous Na$_2$SO$_4$, filtered and concentrated in vacuum. The residue was purified by column chromatography (SiO$_2$, CH$_2$Cl$_2$/MeOH=50:1 to 20:1) to give methyl (2S)-2-[(5-phenylpyrimidin-2-yl)amino]-4-[5-(5,6,7,8-tetrahydro-1,8-naphthyridin-2-yl)pentanoylamino] butanoate (400.00 mg, 639.96 umol, 74.97% yield) as a yellow oil. MS m/z: 503 [M+H]$^+$.

To a solution of methyl (2S)-2-[(5-phenylpyrimidin-2-yl)amino]-4-[5-(5,6,7,8-tetrahydro-1,8-naphthyridin-2-yl)pentanoylamino]butanoate (350.00 mg, 696.36 umol) in THF (8.00 mL) and H$_2$O (2.00 mL) was added LiOH.H$_2$O (87.66 mg, 2.09 mmol) at 25° C., and the reaction was stirred for 2 h at 25° C. The reaction was quenched with H$_2$O (5 mL) and extracted with EtOAc (10 mL*2). The aqueous phase was acidified with aqueous HCl (1 M) to pH=6 and extracted with CH$_2$Cl$_2$ (15 mL*3). The combined organic phase was washed with brine (20 mL*2), dried with anhydrous Na$_2$SO$_4$, filtered, and concentrated in vacuum. The residue was purified by re-crystallization from MeCN (5 mL*2). Then the residue was purified by prep-TLC (SiO$_2$, CH$_2$Cl$_2$:MeOH=10:1) to give (2S)-2-[(5-phenylpyrimidin-2-yl)amino]-4-[5-(5,6,7,8-tetrahydro-1,8-naphthyridin-2-yl)pentanoylamino]butanoic acid Example 92 (50.00 mg, 101.79 umol) as a white solid. MS m/z: 489[M+H]$^+$.

PROCEDURE FOR THE SYNTHESIS OF
EXAMPLES 93 AND 94

2-(3-phenyl-1H-1,2,4-triazol-1-yl)-4-(5-(5,6,7,8-tetrahydro-1,8-naphthyridin-2-yl)pentanamido)butanoic acid (93 mg) was separated to two optical isomers (S or R) by prep-HPLC (column: AD(250 mm*30 mm, 10 um)). The pH of the fraction obtained by HPLC was adjusted to 5 by progressively adding 0.5 M HCl. The pH was adjusted to 7 by progressively adding sat. NaHCO$_3$. The mixture was extracted with 20 mL*2 (CH$_2$Cl$_2$:isopropanol=5:1). The combined organic layers were dried over Na$_2$SO$_4$, filtered and lyophilized to give (S or R)-2-(3-phenyl-1,2,4-triazol-1-yl)-4-[5-(5,6,7,8-tetrahydro-1,8-naphthyridin-2-yl)pentanoylamino]-butanoic acid (50.10 mg, 107.63 umol) as a white solid. MS m/z: 463[M+H]$^+$ and (S or R)-2-(3-phenyl-1,2,4-triazol-1-yl)-4-[5-(5,6,7,8-tetrahydro-1,8-naphthyridin-2-yl)pentanoylamino]butanoic acid (39.60 mg, 84.82 umol) as a white solid. MS m/z: 463[M+H]$^+$.

Compounds in which $R^{10}$ and $R^{11}$ are fluoro may be prepared as described above from the corresponding fluorinated 5-(5,6,7,8-tetrahydro-1,8-naphthyridin-2-yl)pentanoic acid, which is obtainable by methods well known in the art. [See, for example, Bunnelle et al., J. Org. Chem., 1990, 55 (2), :768-770; and Rozen et al., J Org. Chem. 2001, 66 (22):7464-8.]

HEK-293 Cells Expressing αVβ3. HEK-293 cells were transfected using lipofectamine 2000 (Invitrogen #11668030) with the cDNA for αV using the pEF1/V5-His A vector and the cDNA for β3 using the vector pcDNA3.1. Cells expressing αVβ3 were identified by their reaction with murine monoclonal antibodies (mAbs) LM609 and 7E3, and stable cell lines were established by repetitive sorting using LM609. Cells were found to not express αIIbβ3 as judged by negative reaction with mAb 10E5. HEK-293-αVβ3 cells for assays are counted in an automated cell counter (ADVIA 120) and adjusted to values appropriate for each assay.

αVβ3 Cell Adhesion to Fibrinogen Assay. Polystyrene 96-well microtiter plates (Costar, 3590) are precoated with 3.5 μg/mL of purified fibrinogen (Enzyme Research Laboratories) in 0.15 M NaCl, 0.01 M Tris/HCL, pH 7.4 for 1 hour at 37° C. The wells are then washed and incubated with HEPES-Buffered Modified Tyrode's solution (HBMT; 0.128 M NaCl, 10 mM HEPES, 12 mM NaHCO$_3$, 0.4 mM NaH$_2$PO$_4$, 2.7 mM KCl, 0.35% bovine serum albumin (Fisher), 0.1% glucose, pH 7.4) for 1 hour at room temperature or overnight at 4° C. Wells are washed with HBMT containing 1 mM Mg2+ and 2 mM Ca2+ and then 50 μL of HEK-293-αVβ3 cells that have been pretreated with the compound to be tested for 20 minutes at room temperature are added to each well at a concentration of 3,000 cells/μL. After 30-32 minutes the wells are washed with HBMT containing Ca2+ and Mg2+ three times and then the adherent cells are lysed and the acid phosphatase activity that is released is measured by: 1. adding phosphatase substrate (Sigma EC 224-246-5) at 2 mg/mL in 0.1 M Na citrate, pH 5.6, 0.1% triton X-100 for 1 hour at room temperature; 2. stopping the reaction by adding 50 μL of 2 M NaOH; and 3. analyzing the samples in a spectrophotometer at 405 nm. In each assay, 10 mM EDTA is used as a positive control and untreated cells are used as a negative control. The IC$_{50}$ is the dose of test compound that reduces by 50% the adhesion of the HEK-293-αVβ3 cells, taking the results with untreated cells as 100% and the results in the presence of EDTA as 0%. In some instances more than one IC$_{50}$ determination was made, in which case, results of separate determinations are reported. IC50's were not determined for all compounds in the table; for some of these test compounds the inhibition at specific doses are reported. In some instances, the test compound produced a greater reduction than 10 mM EDTA, and these are shown as negative numbers.

AP5 Binding Assay. HEK-293-αVβ3 cells are harvested using 0.05% trypsin 0.5 mM EDTA, washed with HBMT once, and resuspended in HBMT containing 1 mM Mg2+ and 2 mM Ca2+. The cells are counted and adjusted to 0.5×106 cells per sample. The compound to be tested and fluorescently labeled mAb AP5 (either Alexa 488 or Alexa 674; 10 μg/mL) are added and incubated for 30 minutes at 37° C. The cells are then washed and analyzed by flow cytometry (BD FACSCalibur) at the appropriate wavelength for detecting the AP5 fluorophore. In each assay, cilengitide (1 µM) and 10 mM EDTA are included as positive controls and untreated cells are used as the negative control. The concentration of the test compound required to induce the expression of 50% of the AP5 expression induced by cilengitide is calculated and defined as the $EC_{50}$. The $EC_{50}$ for cilengitide was determined based on the expression induced by EDTA. The AP5 expression induced by 1 µM cilengitide was approximately twice the value with 10 mM EDTA (average±SD of 17 experiments; control 7.6±2.2, EDTA 21.8±5.9, cilengitide 42.5±8.0 arbitrary fluorescence units). In cases where even the highest concentration of test compound (10 µM) did not induce 50% exposure of the AP5 epitope, the results are reported as >10 µM and the actual expression induced at the highest concentration is reported in parentheses, e.g., (19%@10 µM).

Results of testing in the foregoing screens are shown in Table 1, wherein the $IC_{50}$s are given in µM:

TABLE 1

| Example | Structure | IC50 | EC50 |
|---|---|---|---|
| 1 | 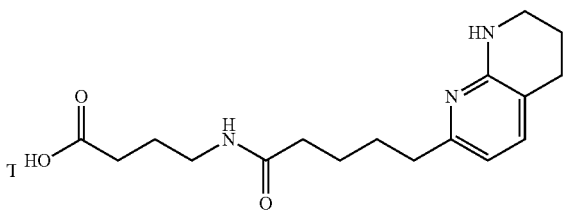 | 1.35 | >100 |
| 2 | 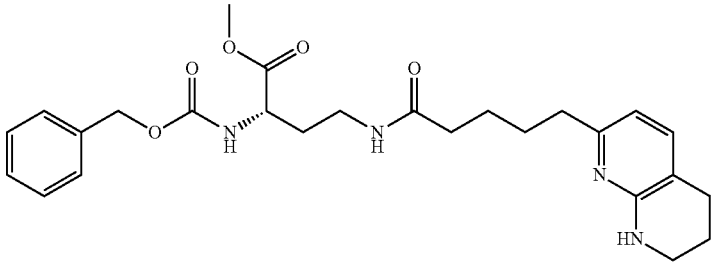 [SMILES: COC(=O)[C@H](CCNC(=O)CCCCc1ccc2c(n1)NCCC2)NC(=O)OCc1ccccc1] | 0.286, 1.68 | >10 (19%@10 µM) |
| 3 | 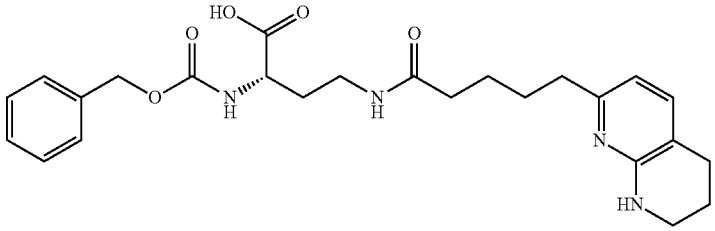 [SMILES: O=C(CCCCc1ccc2c(n1)NCCC2)NCC[C@H](NC(=O)OCc1ccccc1)C(=O)O] | 0.146, 0.484, 0.699, 0.362, 0.324, 0.344 | >10 (16%, 23%, 24%@10 µM) |
| 4 | 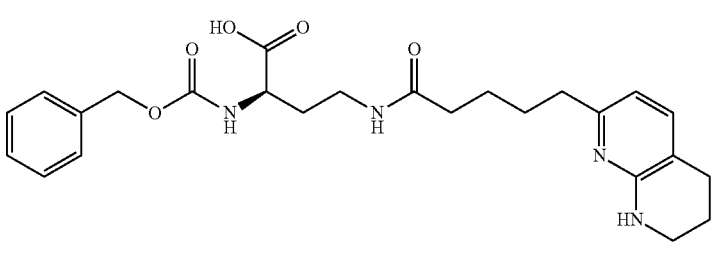 [SMILES: O=C(CCCCc1ccc2c(n1)NCCC2)NCC[C@@H](NC(=O)OCc1ccccc1)C(=O)O] | 0.225, 0.773, 0.952, 0.537, 0.612, 0.683 | >10 (5%, 8%, 5%@10 µM) |
| 5 | 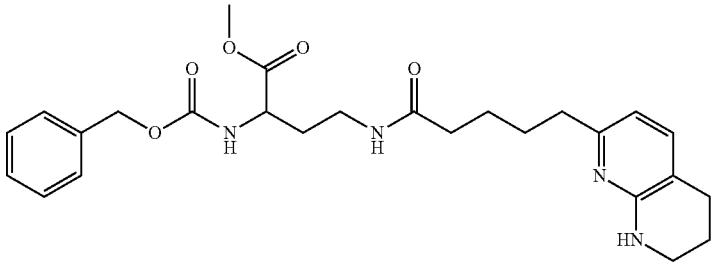 [SMILES: COC(=O)C(CCNC(=O)CCCCc1ccc2c(n1)NCCC2)NC(=O)OCc1ccccc1] | 2.45 | >10 (23%@10 µM) |

TABLE 1-continued

| Example | Structure | IC50 | EC50 |
|---|---|---|---|
| 6 | 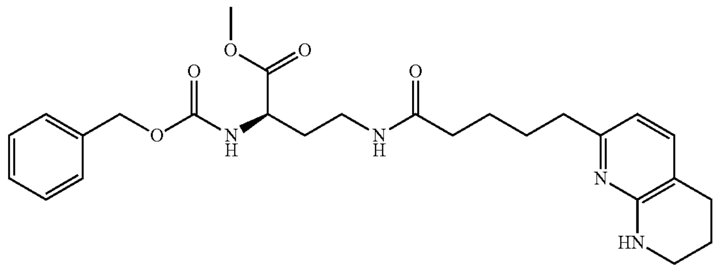 [SMILES: COC(=O)[C@@H](CCNC(=O)CCCCc1ccc2c(n1)NCCC2)NC(=O)OCc1ccccc1] | >10.0 | N.D. |
| 7 | 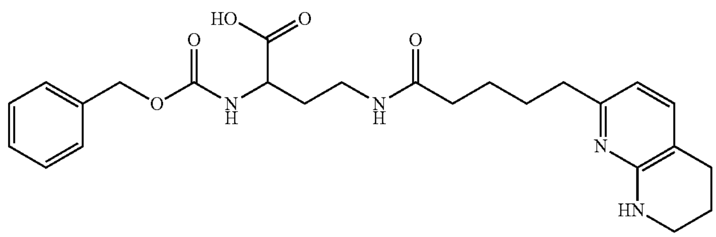 [SMILES: O=C(CCCCc1ccc2c(n1)NCCC2)NCCC(NC(=O)OCc1ccccc1)C(=O)O] | 0.407, 0.57, 0.337, 0.428 | >10 (15%@10 μM) |
| 8 | 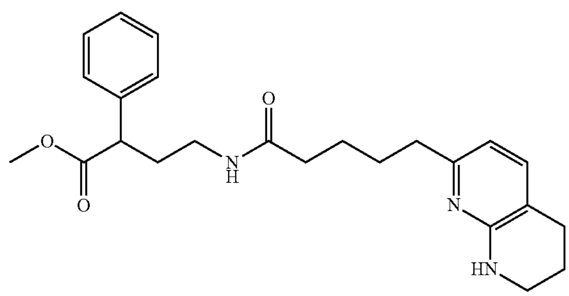 [SMILES: COC(=O)C(CCNC(=O)CCCCc1ccc2c(n1)NCCC2)c1ccccc1] | >10.0 | N.D. |
| 9 | 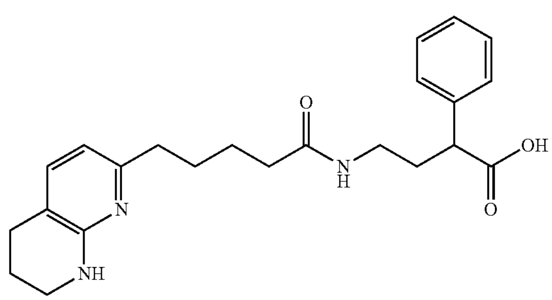 [SMILES: O=C(CCCCc1ccc2c(n1)NCCC2)NCCC(C(=O)O)c1ccccc1] | 3.72, 1.77 | >10 (11%@10 μM) |
| 10 | 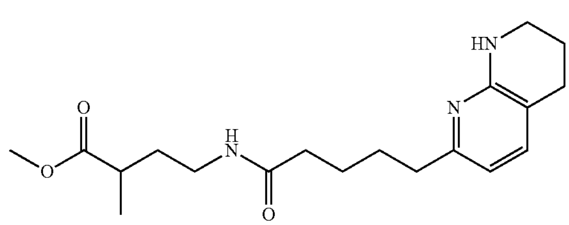 [SMILES: COC(=O)C(C)CCNC(=O)CCCCc1ccc2c(n1)NCCC2] | >10.0 | N.D. |

TABLE 1-continued

| Example | Structure | IC50 | EC50 |
|---|---|---|---|
| 11 | 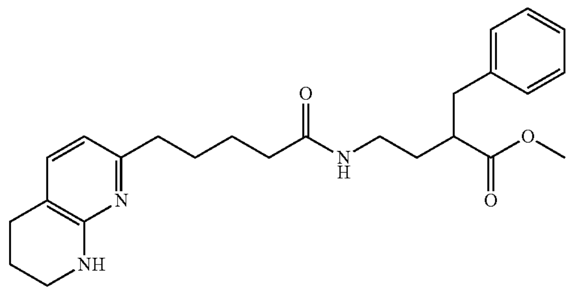 [SMILES: COC(=O)C(CCNC(=O)CCCCc1ccc2c(n1)NCCC2)Cc1ccccc1] | >10.0 | N.D. |
| 12 | 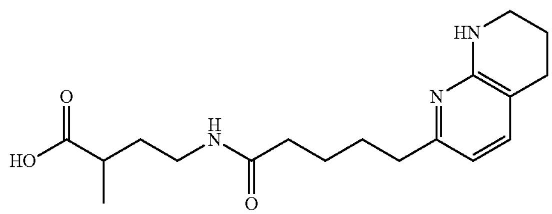 [SMILES: CC(CCNC(=O)CCCCc1ccc2c(n1)NCCC2)C(=O)O] | >10.0 | N.D. |
| 13 | 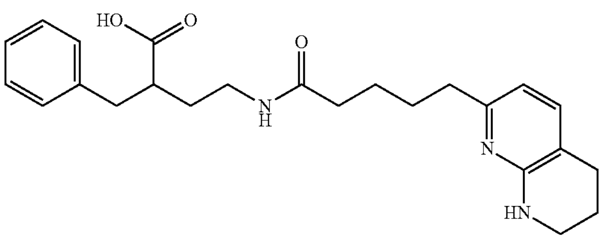 [SMILES: O=C(CCCCc1ccc2c(n1)NCCC2)NCCC(Cc1ccccc1)C(=O)O] | >10.0 | N.D. |
| 14 | 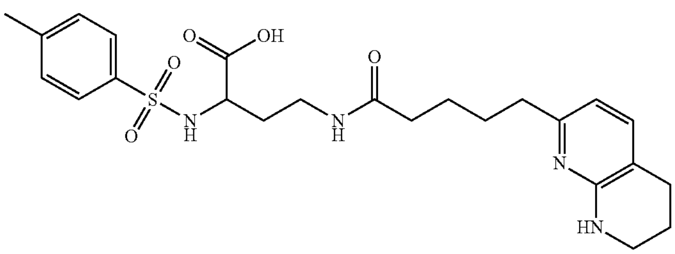 [SMILES: Cc1ccc(S(=O)(=O)NC(CCNC(=O)CCCCc2ccc3c(n2)NCCC3)C(=O)O)cc1] | 6.3 | >10 (7%@10 μM) |
| 15 | 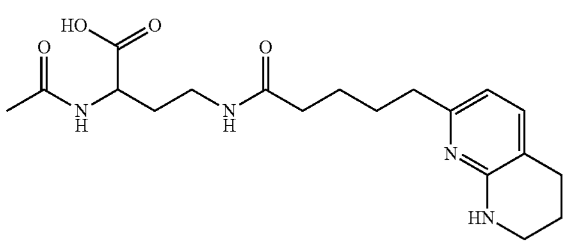 [SMILES: CC(=O)NC(CCNC(=O)CCCCc1ccc2c(n1)NCCC2)C(=O)O] | 1 (−45%)-10 (92%) | |
| 16 | 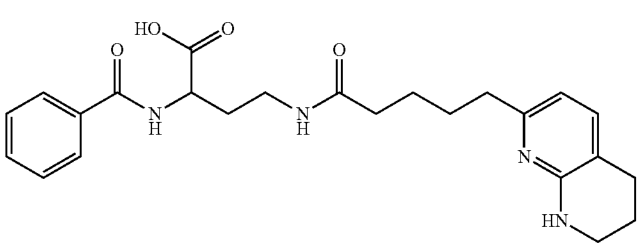 [SMILES: O=C(CCCCc1ccc2c(n1)NCCC2)NCCC(NC(=O)c1ccccc1)C(=O)O] | 1 (26%)-10 (95%) | |

| Example | Structure | IC50 | EC50 |
|---|---|---|---|
| 17 | 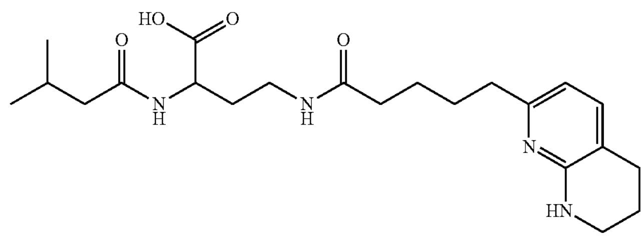 [SMILES: CC(C)CC(=O)NC(CCNC(=O)CCCCc1ccc2c(n1)NCCC2)C(=O)O] | 1 (−22%)-<br>10 (90%) | |
| 18 | 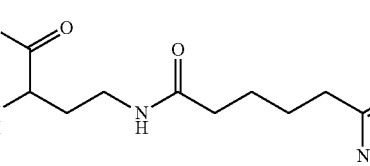 | 1 (−29%)-<br>10 (92%) | |
| 19 | 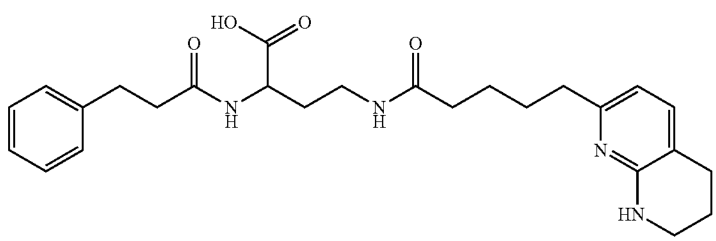 [SMILES: O=C(CCCCc1ccc2c(n1)NCCC2)NCCC(NC(=O)CCc1ccccc1)C(=O)O] | 1 (−15%)-<br>10 (96%) | |
| 20 | 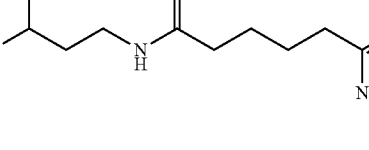 | 1 (−12%)-<br>10 (99%) | |
| 21 | 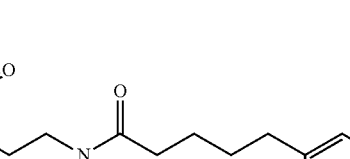 | 1 (−37%)-<br>10 (96%) | |
| 22 | 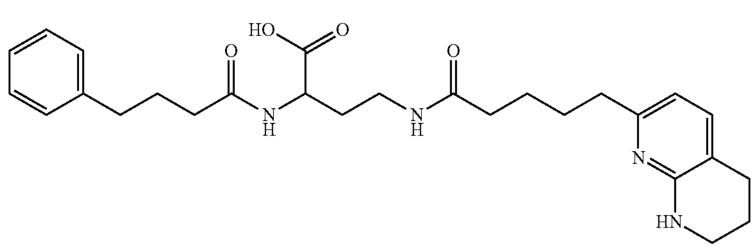 [SMILES: O=C(CCCCc1ccc2c(n1)NCCC2)NCCC(NC(=O)CCCc1ccccc1)C(=O)O] | 1 (−25%)-<br>10 (98%) | |

TABLE 1-continued

| Example | Structure | IC50 | EC50 |
| --- | --- | --- | --- |
| 23 | 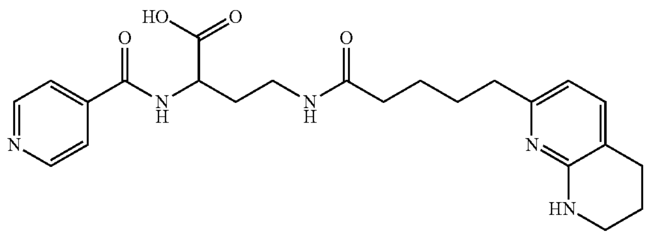 [SMILES: O=C(CCCCc1ccc2c(n1)NCCC2)NCCC(NC(=O)c1ccncc1)C(=O)O] | 1 (29%)-10 (99%) | |
| 24 | 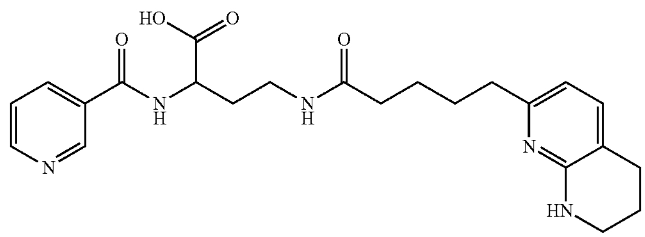 [SMILES: O=C(CCCCc1ccc2c(n1)NCCC2)NCCC(NC(=O)c1cccnc1)C(=O)O] | 1 (22%)-10 (97%) | |
| 25 | 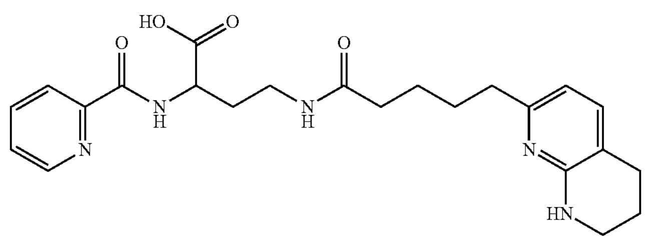 [SMILES: O=C(CCCCc1ccc2c(n1)NCCC2)NCCC(NC(=O)c1ccccn1)C(=O)O] | <0.10 | >10 (16%@10 μM) |
| 26 | 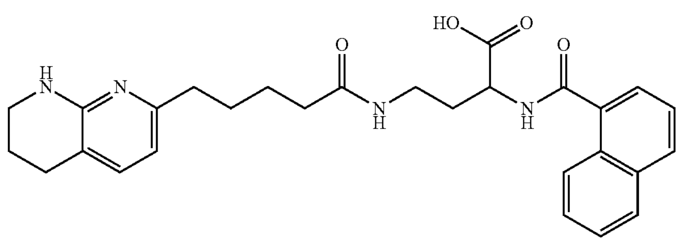 [SMILES: O=C(CCCCc1ccc2c(n1)NCCC2)NCCC(NC(=O)c1cccc2ccccc12)C(=O)O] | 1 (37%)-10 (101%) | |
| 27 | 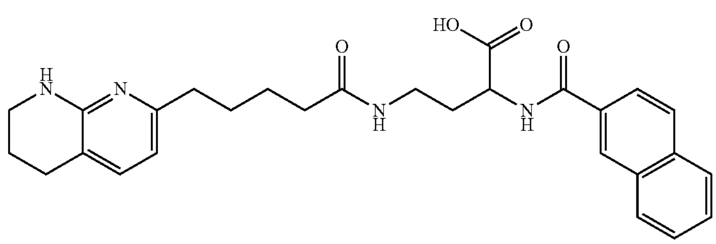 [SMILES: O=C(CCCCc1ccc2c(n1)NCCC2)NCCC(NC(=O)c1ccc2ccccc2c1)C(=O)O] | 1 (35%)-10 (101%) | |
| 28 | 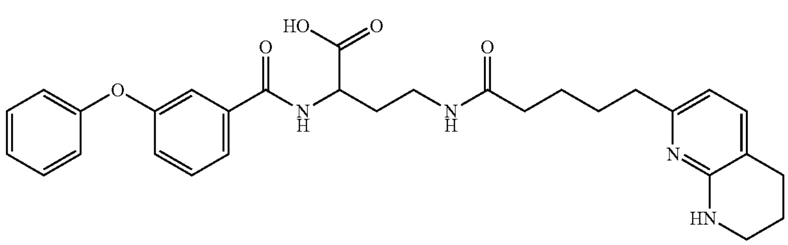 [SMILES: O=C(CCCCc1ccc2c(n1)NCCC2)NCCC(NC(=O)c1cccc(Oc2ccccc2)c1)C(=O)O] | 1 (−6%)-10 (98%) | |

TABLE 1-continued

| Example | Structure | IC50 | EC50 |
|---|---|---|---|
| 29 | 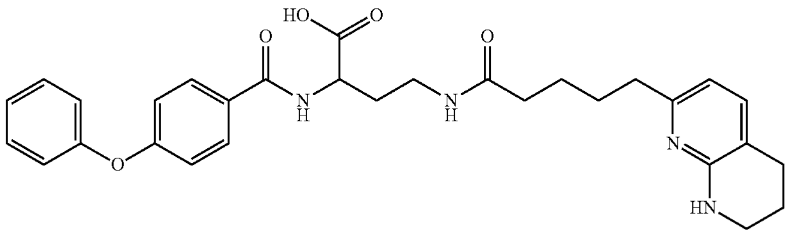 [SMILES: O=C(CCCCc1ccc2c(n1)NCCC2)NCCC(NC(=O)c1ccc(Oc2ccccc2)cc1)C(=O)O] | 1 (−63%)-10 (96%) | |
| 30 | 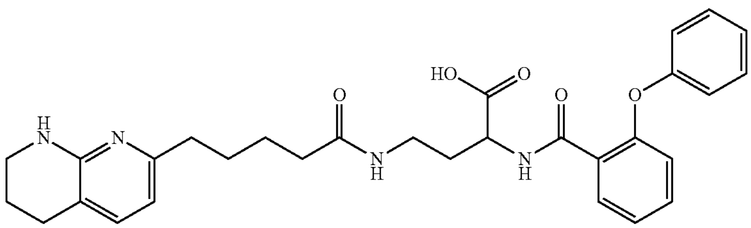 [SMILES: O=C(CCCCc1ccc2c(n1)NCCC2)NCCC(NC(=O)c1ccccc1Oc1ccccc1)C(=O)O] | 1 (−41%)-10 (92%) | |
| 31 | 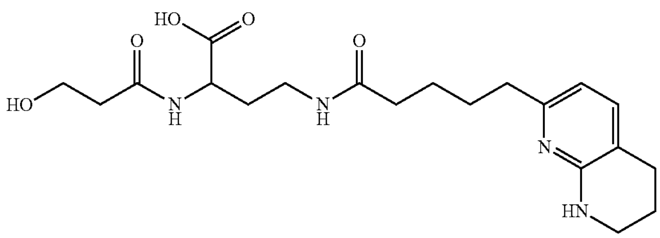 [SMILES: O=C(CCCCc1ccc2c(n1)NCCC2)NCCC(NC(=O)CCO)C(=O)O] | 1 (−17%)-10 (68%) | |
| 32 | 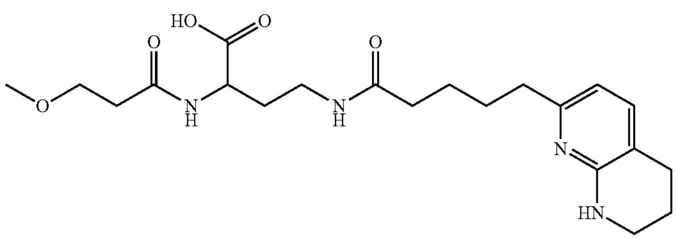 [SMILES: COCCC(=O)NC(CCNC(=O)CCCCc1ccc2c(n1)NCCC2)C(=O)O] | 1 (14%)-10 (88%) | |
| 33 | 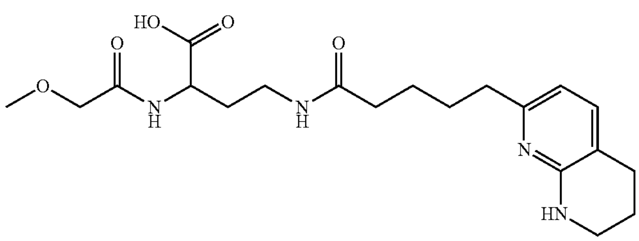 [SMILES: COCC(=O)NC(CCNC(=O)CCCCc1ccc2c(n1)NCCC2)C(=O)O] | 1 (18%)-10 (100%) | |
| 34 | 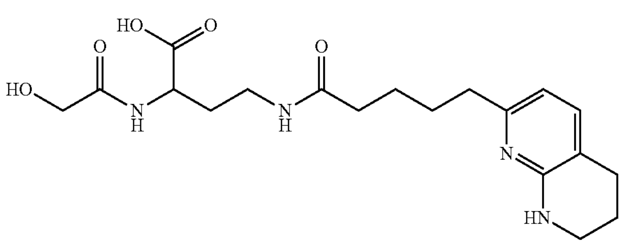 [SMILES: O=C(CCCCc1ccc2c(n1)NCCC2)NCCC(NC(=O)CO)C(=O)O] | <0.10 | >10 (32%@10 μM) |
| 35 | 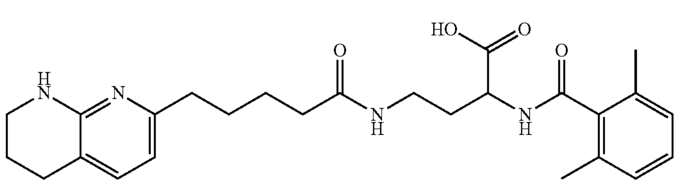 [SMILES: Cc1cccc(C)c1C(=O)NC(CCNC(=O)CCCCc1ccc2c(n1)NCCC2)C(=O)O] | 1 (39%)-10 (66%) | |

TABLE 1-continued

| Example | Structure | IC50 | EC50 |
| --- | --- | --- | --- |
| 36 | 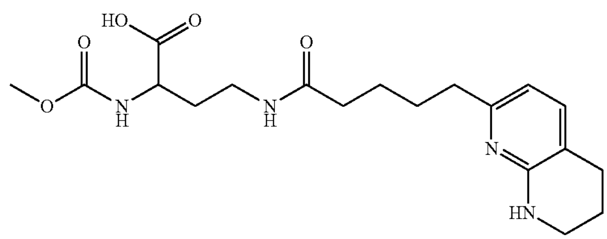 [SMILES: COC(=O)NC(CCNC(=O)CCCCc1ccc2c(n1)NCCC2)C(=O)O] | <0.10 | >10 (12%@10 µM) |
| 37 | 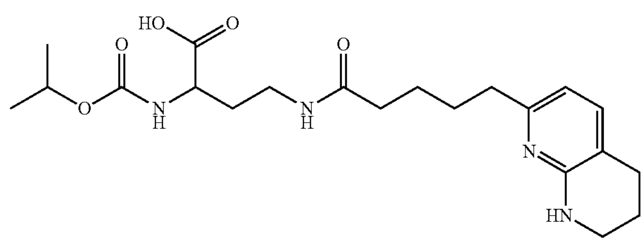 [SMILES: CC(C)OC(=O)NC(CCNC(=O)CCCCc1ccc2c(n1)NCCC2)C(=O)O] | 1 (48%)-10 (99%) | |
| 38 | 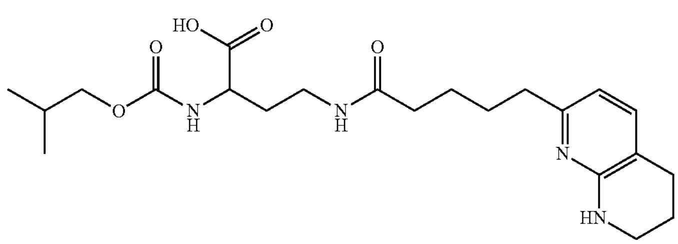 [SMILES: CC(C)COC(=O)NC(CCNC(=O)CCCCc1ccc2c(n1)NCCC2)C(=O)O] | 0.343 0.416 | >10 (20%, 14%, 19%@10 µM) |
| 39 | 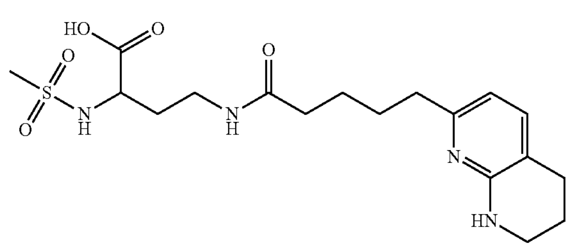 [SMILES: CS(=O)(=O)NC(CCNC(=O)CCCCc1ccc2c(n1)NCCC2)C(=O)O] | 1 (−13%)-10 (73%) | |
| 40 | 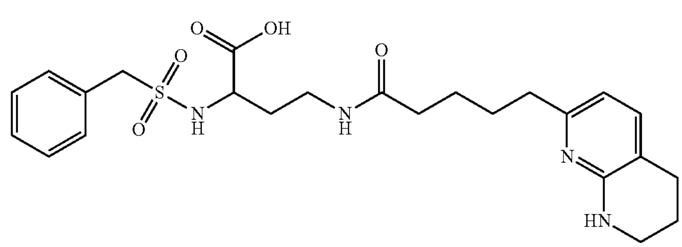 [SMILES: O=C(CCCCc1ccc2c(n1)NCCC2)NCCC(NS(=O)(=O)Cc1ccccc1)C(=O)O] | 1 (1%)-10 (77%) | |
| 41 | 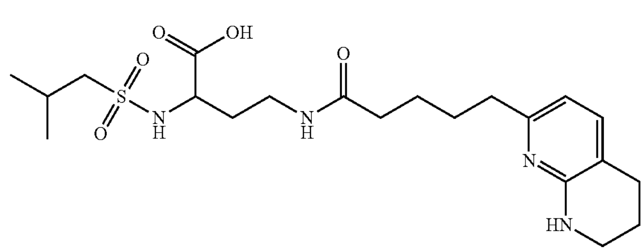 [SMILES: CC(C)CS(=O)(=O)NC(CCNC(=O)CCCCc1ccc2c(n1)NCCC2)C(=O)O] | 1 (9%)-10 (98%) | |

TABLE 1-continued
| Example | Structure | IC50 | EC50 |
|---|---|---|---|
| 42 | 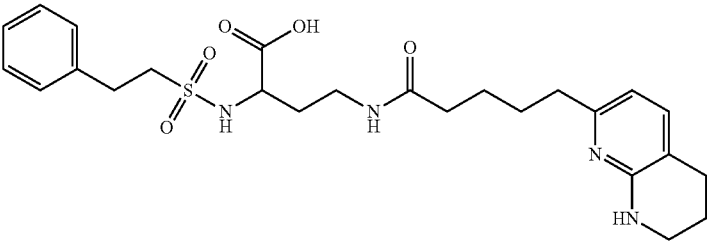 [SMILES: O=C(CCCCc1ccc2c(n1)NCCC2)NCCC(NS(=O)(=O)CCc1ccccc1)C(=O)O] | 1 (44%)-<br>10 (97%) | |
| 43 | 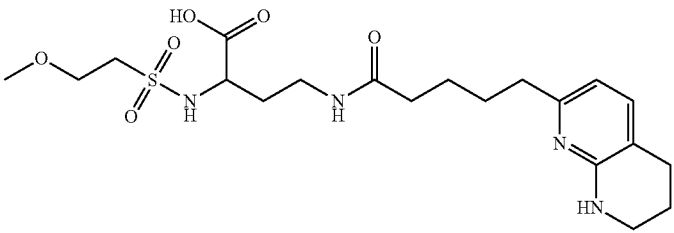 [SMILES: COCCS(=O)(=O)NC(CCNC(=O)CCCCc1ccc2c(n1)NCCC2)C(=O)O] | 1 (17%)-<br>10 (97%) | |
| 44 | 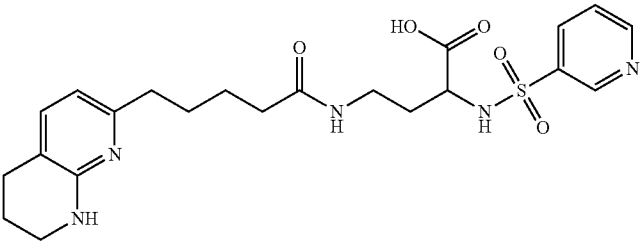 [SMILES: O=C(CCCCc1ccc2c(n1)NCCC2)NCCC(NS(=O)(=O)c1cccnc1)C(=O)O] | 0.1 (40%)-<br>1 (65%)<br>1.33 | >10 (22%,<br>16%@10 μM) |
| 45 | 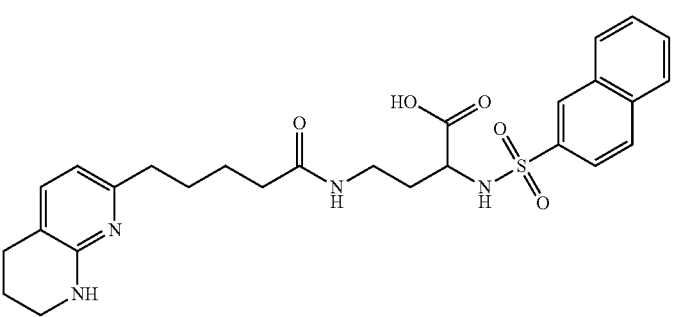 [SMILES: O=C(CCCCc1ccc2c(n1)NCCC2)NCCC(NS(=O)(=O)c1ccc2ccccc2c1)C(=O)O] | 0.1 (40%)-<br>1 (65%) | |
| 46 | 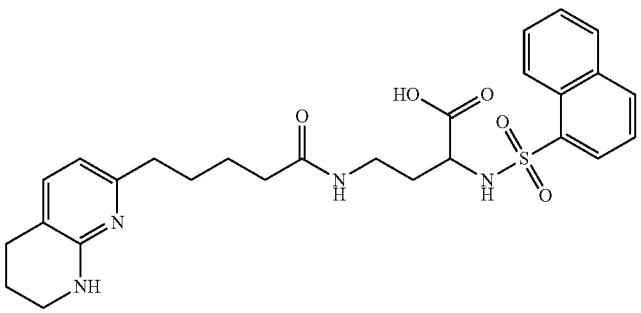 [SMILES: O=C(CCCCc1ccc2c(n1)NCCC2)NCCC(NS(=O)(=O)c1cccc2ccccc12)C(=O)O] | 1 (42%)-<br>10 (99%) | |

TABLE 1-continued
| Example | Structure | IC50 | EC50 |
|---|---|---|---|
| 47 | 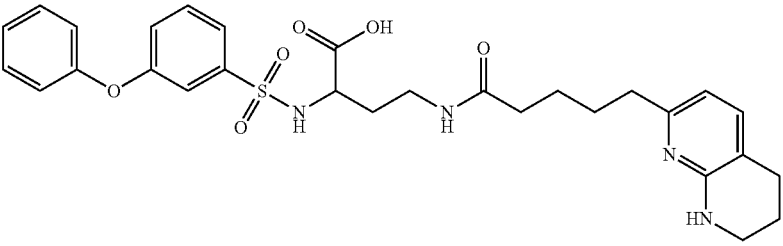 [SMILES: O=C(CCCCc1ccc2c(n1)NCCC2)NCCC(NS(=O)(=O)c1cccc(Oc2ccccc2)c1)C(=O)O] | 1 (−37%)-<br>10 (100%) | |
| 48 | 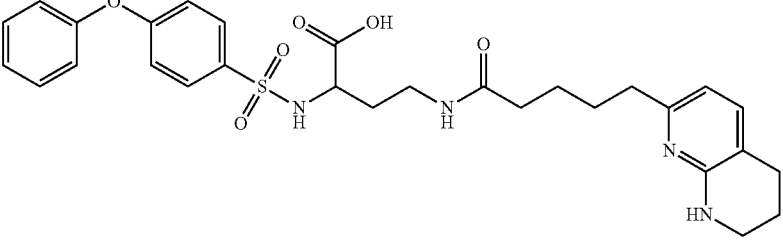 | >10.0 | |
| 49 | 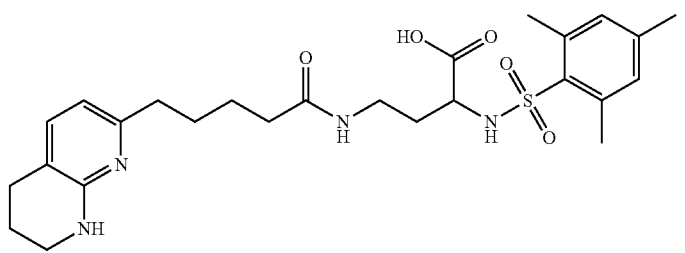 [SMILES: Cc1cc(C)c(S(=O)(=O)NC(CCNC(=O)CCCCc2ccc3c(n2)NCCC3)C(=O)O)c(C)c1] | 1 (19%)-<br>10 (95%) | |
| 50 | 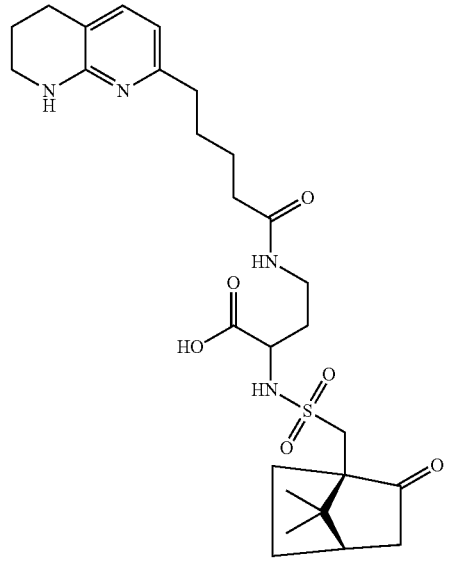 [SMILES: CC1(C)[C@@H]2CC[C@]1(CS(=O)(=O)NC(CCNC(=O)CCCCc1ccc3c(n1)NCCC3)C(=O)O)C(=O)C2] | <0.10 | >10<br>(16%@10 μM) |
| 51 | 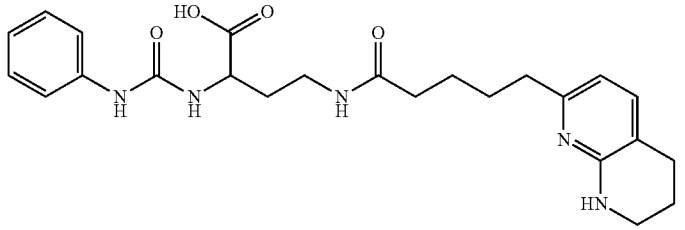 [SMILES: O=C(CCCCc1ccc2c(n1)NCCC2)NCCC(NC(=O)Nc1ccccc1)C(=O)O] | 1 (−16%)-<br>10 (98%) | |

TABLE 1-continued

| Example | Structure | IC50 | EC50 |
| --- | --- | --- | --- |
| 52 | 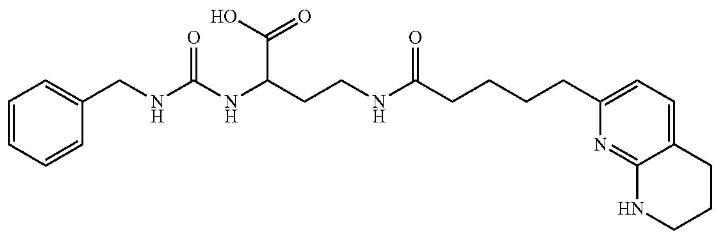 [SMILES: O=C(CCCCc1ccc2c(n1)NCCC2)NCCC(NC(=O)NCc1ccccc1)C(=O)O] | 1 (−9%)-10 (98%) | |
| 53 | 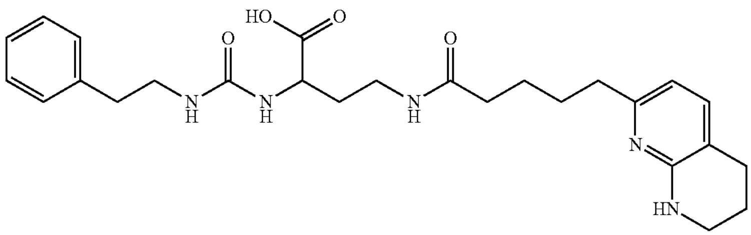 [SMILES: O=C(CCCCc1ccc2c(n1)NCCC2)NCCC(NC(=O)NCCc1ccccc1)C(=O)O] | 1 (−14%)-10 (96%) | |
| 54 | 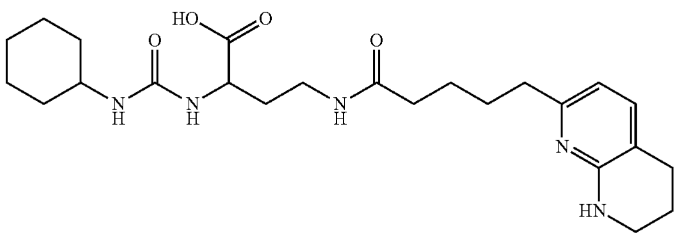 [SMILES: O=C(CCCCc1ccc2c(n1)NCCC2)NCCC(NC(=O)NC1CCCCC1)C(=O)O] | 1 (−16%)-10 (98%) | |
| 55 | 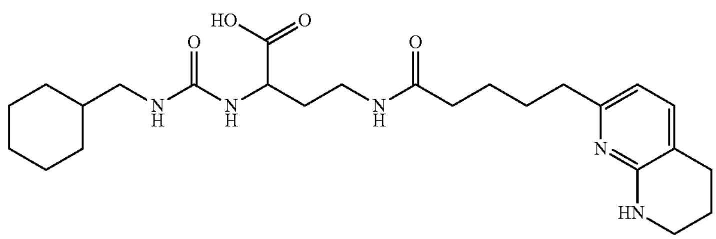 [SMILES: O=C(CCCCc1ccc2c(n1)NCCC2)NCCC(NC(=O)NCC1CCCCC1)C(=O)O] | 1 (−2%)-10 (99%) | |
| 56 | 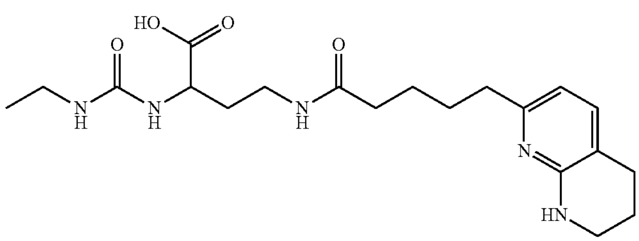 [SMILES: CCNC(=O)NC(CCNC(=O)CCCCc1ccc2c(n1)NCCC2)C(=O)O] | 1 (23%)-10 (96%) | |
| 57 | 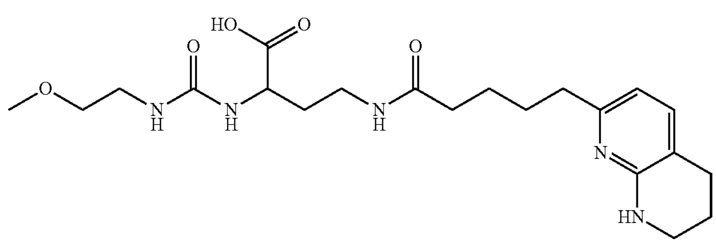 [SMILES: COCCNC(=O)NC(CCNC(=O)CCCCc1ccc2c(n1)NCCC2)C(=O)O] | 1 (16%)-10 (98%) | |

TABLE 1-continued

| Example | Structure | IC50 | EC50 |
|---|---|---|---|
| 58 | 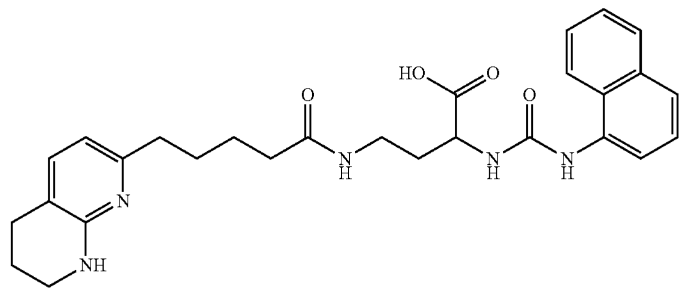 [SMILES: O=C(CCCCc1ccc2c(n1)NCCC2)NCCC(NC(=O)Nc1cccc2ccccc12)C(=O)O] | 1 (16%)-10 (99%) | |
| 59 | 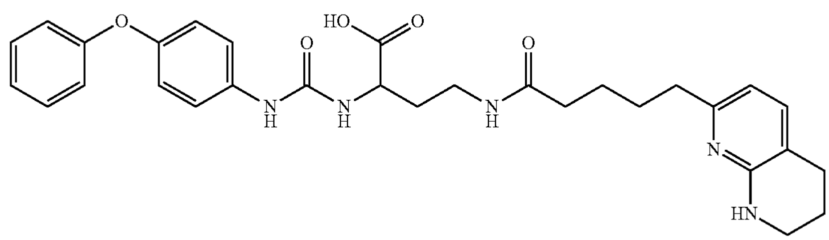 [SMILES: O=C(CCCCc1ccc2c(n1)NCCC2)NCCC(NC(=O)Nc1ccc(Oc2ccccc2)cc1)C(=O)O] | >10.0 | |
| 60 | 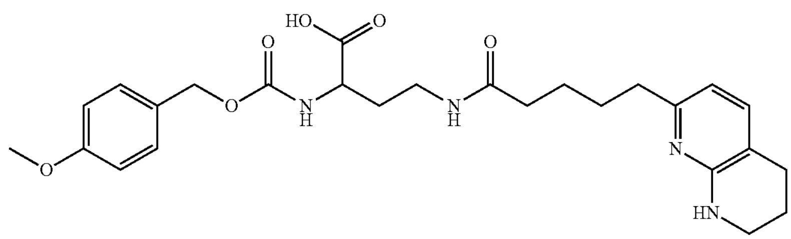 [SMILES: COc1ccc(COC(=O)NC(CCNC(=O)CCCCc2ccc3c(n2)NCCC3)C(=O)O)cc1] | 0.579 | >10 (10%@10 μM) |
| 61 | 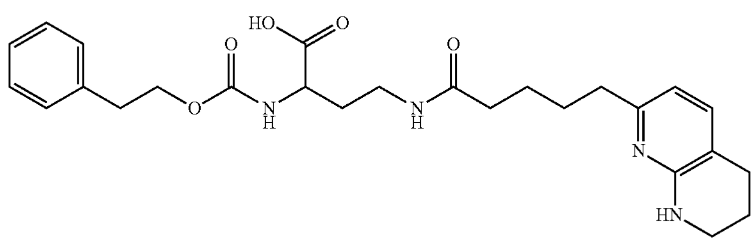 [SMILES: O=C(CCCCc1ccc2c(n1)NCCC2)NCCC(NC(=O)OCCc1ccccc1)C(=O)O] | 0.586 | >10 (14%@10 μM) |
| 62 | 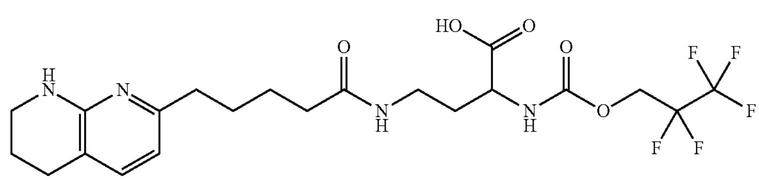 [SMILES: O=C(CCCCc1ccc2c(n1)NCCC2)NCCC(NC(=O)OCC(F)(F)C(F)(F)F)C(=O)O] | 0.628 | >10 (12%@10 μM) |
| 63 | 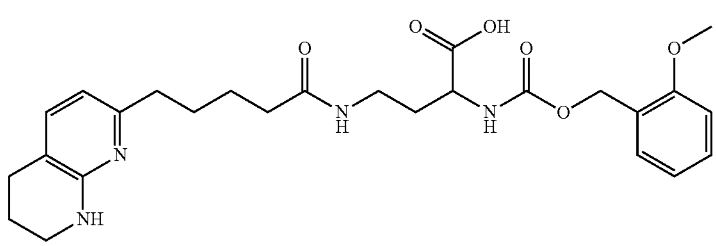 [SMILES: COc1ccccc1COC(=O)NC(CCNC(=O)CCCCc1ccc2c(n1)NCCC2)C(=O)O] | 0.491 | >10 (16%@10 μM) |

TABLE 1-continued

| Example | Structure | IC50 | EC50 |
| --- | --- | --- | --- |
| 64 | 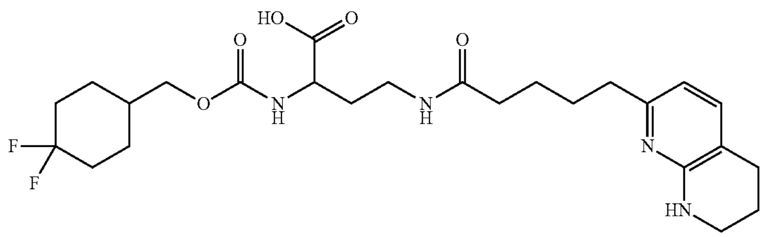 [SMILES: O=C(CCCCc1ccc2c(n1)NCCC2)NCCC(NC(=O)OCC1CCC(F)(F)CC1)C(=O)O] | 0.248, 0.359 | >10 (21%@10 μM) |
| 65 | 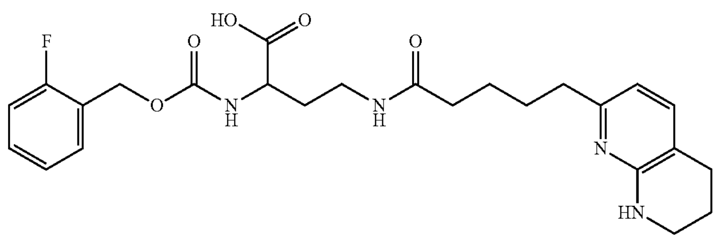 [SMILES: O=C(CCCCc1ccc2c(n1)NCCC2)NCCC(NC(=O)OCc1ccccc1F)C(=O)O] | 0.12 | >10 (13%@10 μM) |
| 66 | 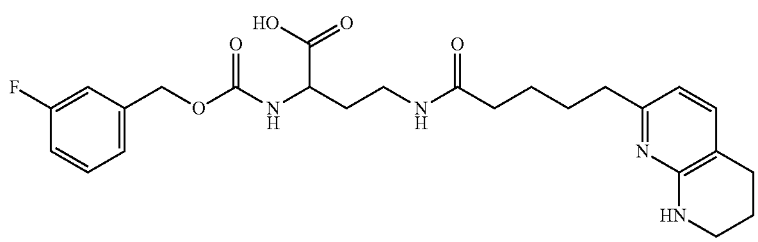 [SMILES: O=C(CCCCc1ccc2c(n1)NCCC2)NCCC(NC(=O)OCc1cccc(F)c1)C(=O)O] | 0.533 | >10 (12%@10 μM) |
| 67 | 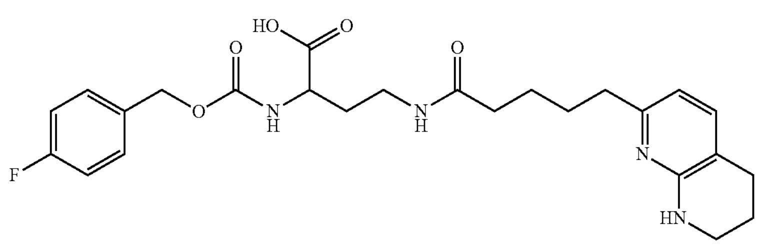 [SMILES: O=C(CCCCc1ccc2c(n1)NCCC2)NCCC(NC(=O)OCc1ccc(F)cc1)C(=O)O] | 0.32 | >10 (13%@10 μM) |
| 68 | 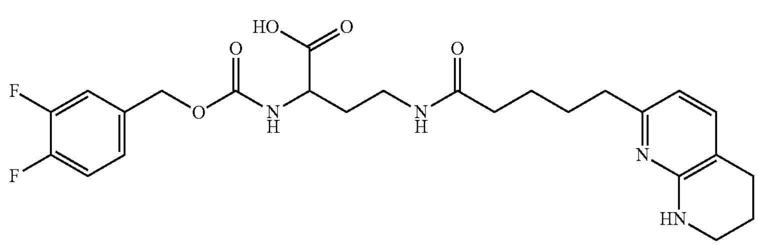 [SMILES: O=C(CCCCc1ccc2c(n1)NCCC2)NCCC(NC(=O)OCc1ccc(F)c(F)c1)C(=O)O] | 0.32 | >10 (9%@10 μM) |
| 69 | 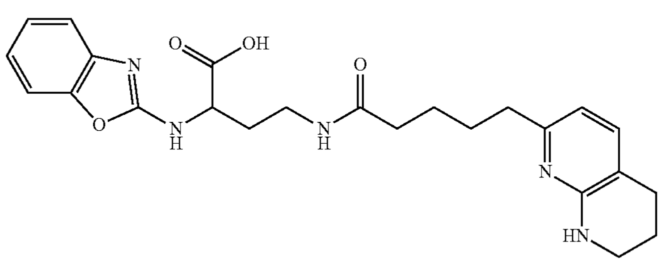 | 0.211 | >10 (7%@10 μM) |

TABLE 1-continued

| Example | Structure | IC50 | EC50 |
| --- | --- | --- | --- |
| 70 | 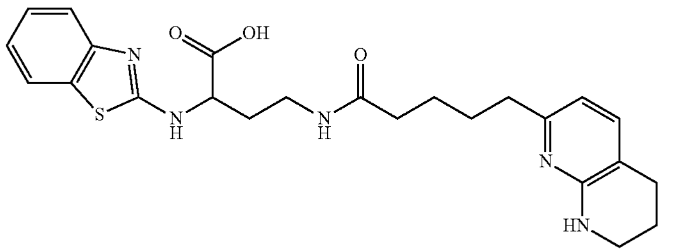 [SMILES: O=C(CCCCc1ccc2c(n1)NCCC2)NCCC(Nc1nc2ccccc2s1)C(=O)O] | 0.525 | >10 (6%@10 μM) |
| 71 | 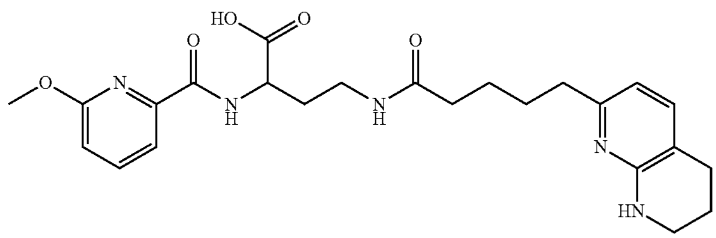 [SMILES: COc1cccc(C(=O)NC(CCNC(=O)CCCCc2ccc3c(n2)NCCC3)C(=O)O)n1] | 1.14 | >10 (9%@10 μM) |
| 72 | 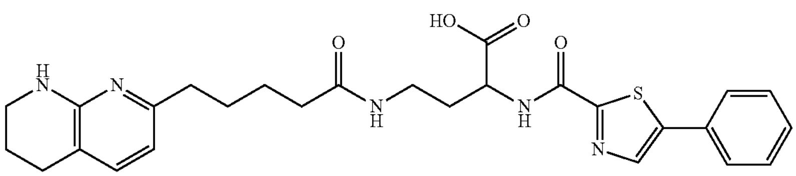 [SMILES: O=C(CCCCc1ccc2c(n1)NCCC2)NCCC(NC(=O)c1ncc(-c2ccccc2)s1)C(=O)O] | 0.181, 0.0904, 0.185 | >10 (6%@10 μM) |
| 73 | 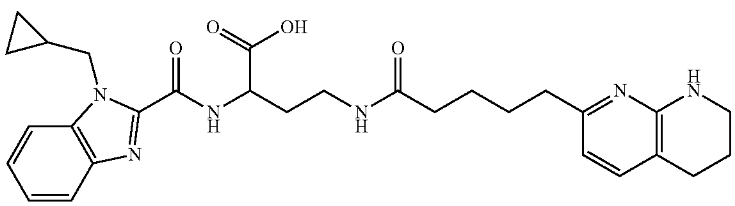 [SMILES: O=C(CCCCc1ccc2c(n1)NCCC2)NCCC(NC(=O)c1nc2ccccc2n1CC1CC1)C(=O)O] | 0.502, 0.142 | >10 (2.5%@10 μM) |
| 74 | 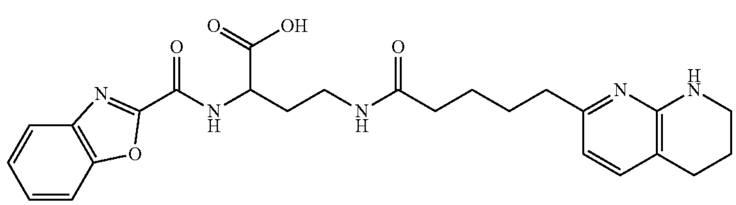 | 0.115 | >10 (4%@10 μM) |
| 75 | 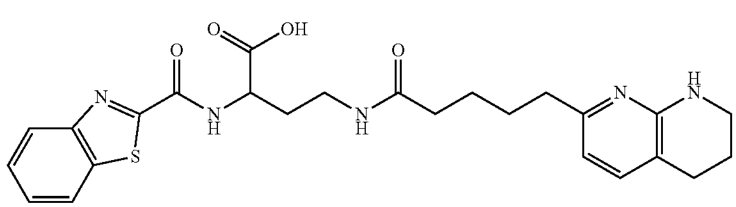 [SMILES: O=C(CCCCc1ccc2c(n1)NCCC2)NCCC(NC(=O)c1nc2ccccc2o1)C(=O)O] | <0.100, 0.0546, 0.0651 | >10 (9%@10 μM) |

TABLE 1-continued
| Example | Structure | IC50 | EC50 |
|---|---|---|---|
| 76 | 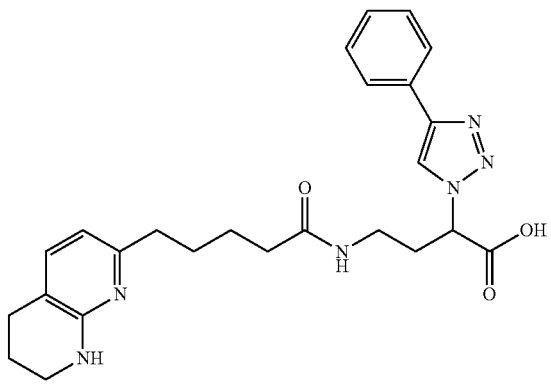 [SMILES: O=C(CCCCc1ccc2c(n1)NCCC2)NCCC(C(=O)O)n1cc(-c2ccccc2)nn1] | 0.939 | >10 (9%@10 μM) |
| 77 | 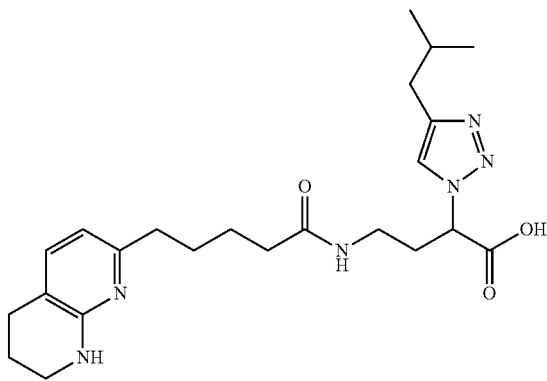 [SMILES: CC(C)Cc1cn(C(CCNC(=O)CCCCc2ccc3c(n2)NCCC3)C(=O)O)nn1] | 2.02 | >10 (8%@10 μM) |
| 78 | 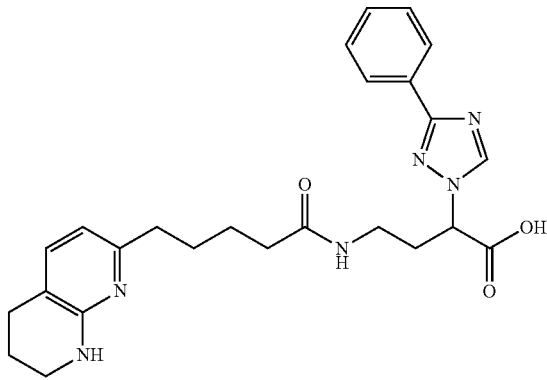 [SMILES: O=C(CCCCc1ccc2c(n1)NCCC2)NCCC(C(=O)O)n1cnc(-c2ccccc2)n1] | 0.518 | >10 (10%@10 μM) |
| 79 | 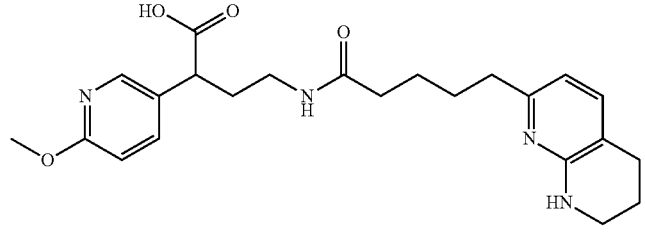 [SMILES: COc1ccc(C(CCNC(=O)CCCCc2ccc3c(n2)NCCC3)C(=O)O)cn1] | 0.532 | >10 (19%@10 μM) |

TABLE 1-continued

| Example | Structure | IC50 | EC50 |
|---|---|---|---|
| 80 | 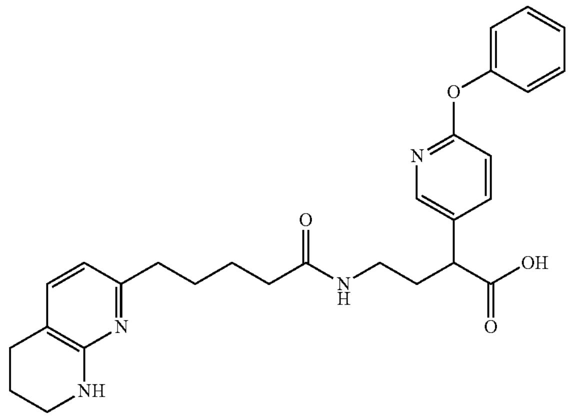 [SMILES: O=C(CCCCc1ccc2c(n1)NCCC2)NCCC(C(=O)O)c1ccc(Oc2ccccc2)nc1] | 1.57, 0.429 | >10 (7.5%@10 μM) |
| 81 | 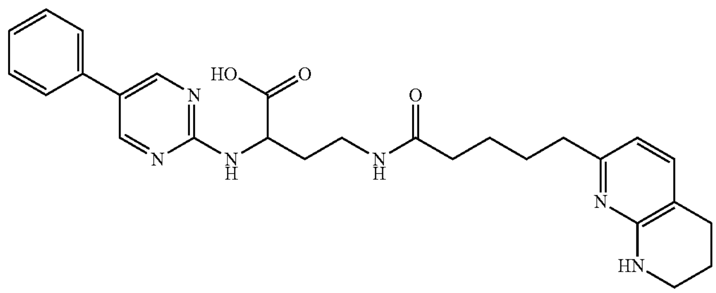 [SMILES: O=C(CCCCc1ccc2c(n1)NCCC2)NCCC(Nc1ncc(-c2ccccc2)cn1)C(=O)O] | <0.100, 0.101, 0.143 | >10 (9%@10 μM) |
| 82 | 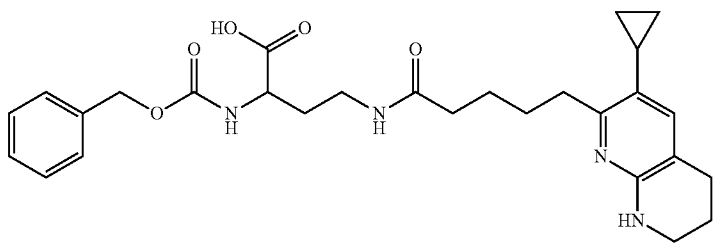 [SMILES: O=C(CCCCc1nc2c(cc1C1CC1)CCCN2)NCCC(NC(=O)OCc1ccccc1)C(=O)O] | 0.206 | >10 (12%@10 μM) |
| 83 | 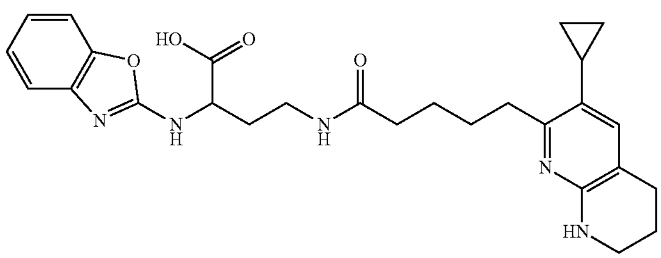 [SMILES: O=C(CCCCc1nc2c(cc1C1CC1)CCCN2)NCCC(Nc1nc2ccccc2o1)C(=O)O] | 0.128 | >10 (5%@10 μM) |
| 84 | 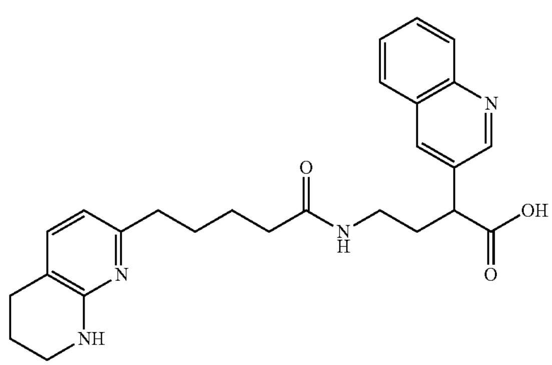 [SMILES: O=C(CCCCc1ccc2c(n1)NCCC2)NCCC(C(=O)O)c1cnc2ccccc2c1] | 0.121 | >10 (31%@10 μM) |

TABLE 1-continued
| Example | Structure | IC50 | EC50 |
| --- | --- | --- | --- |
| 85 | 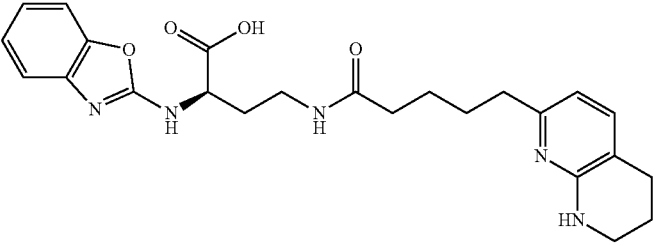 [SMILES: O=C(CCCCc1ccc2c(n1)NCCC2)NCC[C@@H](Nc1nc2ccccc2o1)C(=O)O] | 0.151 | >10 (5%@10 μM) |
| 86 | 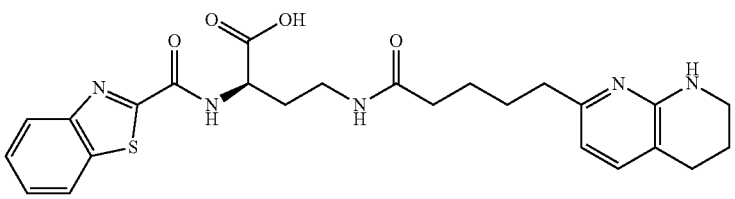 [SMILES: O=C(CCCCc1ccc2c(n1)NCCC2)NCC[C@@H](NC(=O)c1nc2ccccc2s1)C(=O)O] | 0.129, 0.169 | >10 (7%@10 μM) |
| 87 | 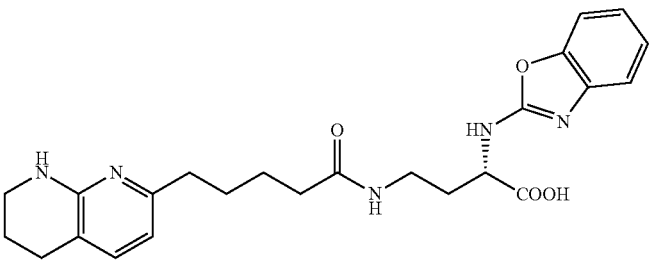 | 0.187 | >10 (14%@10 μM) |
| 88 | 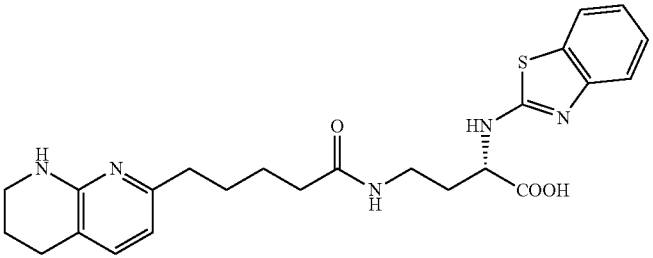 [SMILES: O=C(CCCCc1ccc2c(n1)NCCC2)NCC[C@H](Nc1nc2ccccc2o1)C(=O)O] | 0.0233, 0.0216 | could not be calculated (7%@10 μM) |
| 89 | 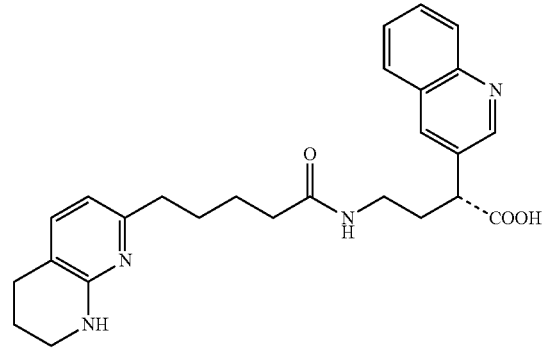 [SMILES: O=C(CCCCc1ccc2c(n1)NCCC2)NCC[C@@H](C(=O)O)c1cnc2ccccc2c1] | 0.106 | >10 (27%@10 μM) |

TABLE 1-continued
| Example | Structure | IC50 | EC50 |
|---|---|---|---|
| 90 | 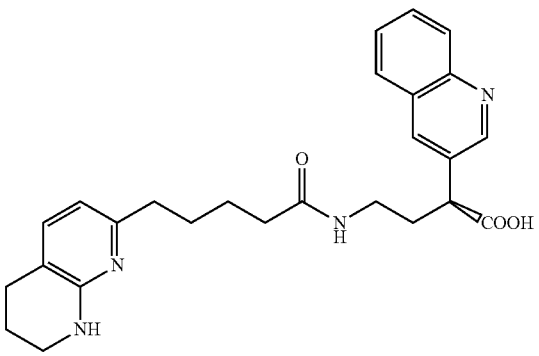 [SMILES: O=C(CCCCc1ccc2c(n1)NCCC2)NCC[C@H](C(=O)O)c1cnc2ccccc2c1] | 0.228 | >10 (11%@10 μM) |
| 91 | 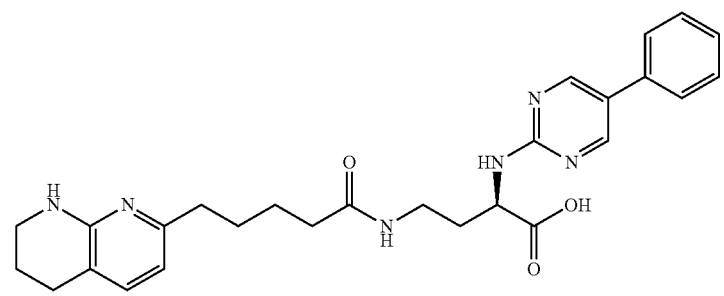 [SMILES: O=C(CCCCc1ccc2c(n1)NCCC2)NCC[C@@H](Nc1ncc(-c2ccccc2)cn1)C(=O)O] | 0.534 | >10 |
| 92 | 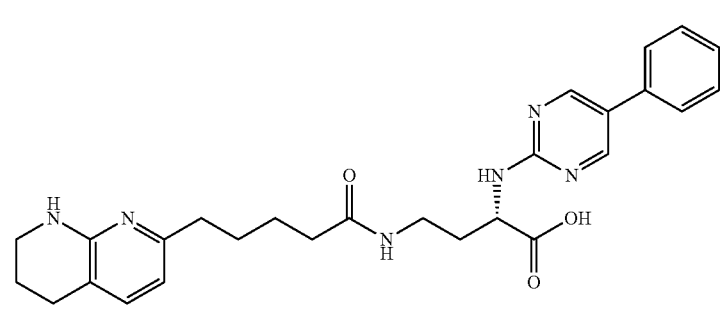 [SMILES: O=C(CCCCc1ccc2c(n1)NCCC2)NCC[C@H](Nc1ncc(-c2ccccc2)cn1)C(=O)O] | 0.201 | >10 |
| 93 | 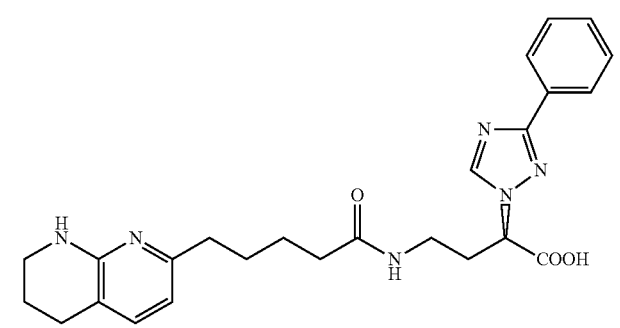 [SMILES: O=C(CCCCc1ccc2c(n1)NCCC2)NCC[C@H](C(=O)O)n1cnc(-c2ccccc2)n1] | 0.288 | >10 |
| 94 | 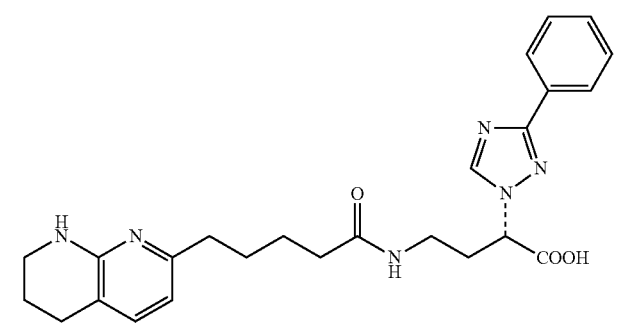 [SMILES: O=C(CCCCc1ccc2c(n1)NCCC2)NCC[C@@H](C(=O)O)n1cnc(-c2ccccc2)n1] | 0.373 | >10 |

The compounds provided herein can be used for treating osteoporosis, acute myelogenous leukemia, sickle cell disease, focal segmental glomerulosclerosis, fibrosis, supravalvular aortic stenosis associated with Williams syndrome, bone resorption, tumors expressing αVβ3, tumor metastasis, T-cell lymphoma, retinal disease, age-related macular degeneration, diabetic retinitis, and herpes simplex virus infection. They may also be used for inhibiting tumor angiogenesis.

The invention claimed is:

1. A compound of formula

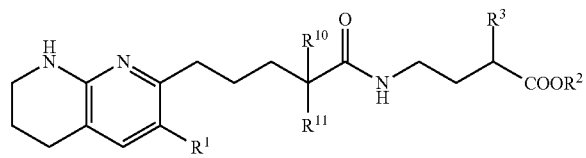

wherein
$R^1$ is hydrogen or $(C_1-C_6)$hydrocarbyl;
$R^2$ is hydrogen or $(C_1-C_6)$hydrocarbyl;
$R^3$ is heterocyclyl optionally substituted with one to three substituents chosen independently from $(C_1-C_{10})$hydrocarbyl, halogen, $(C_1-C_6)$haloalkyl, $(C_1-C_6)$acyl, hydroxy$(C_1-C_6)$loweralkyl, benzenesulfonyl, hydroxy, halo$(C_1-C_6)$alkoxy, $(C_1-C_6)$oxaalkyl, carboxy, $(C_1-C_6)$alkoxycarbonyl, carboxamido, cyano, acetoxy, nitro, amino, $(C_1-C_6)$alkylamino, di$(C_1-C_6)$alkylamino, $(C_1-C_6)$alkylthio, $(C_1-C_6)$alkylsulfonylamino, $(C_1-C_6)$alkylsulfinyl, $(C_1-C_6)$alkylsulfonyl, heterocyclyl, and $(C_1-C_{10})$hydrocarbyloxy; and
$R^{10}$ and $R^{11}$ are chosen independently from hydrogen and fluoro.

2. A compound according to claim 1 wherein $R^3$ is heterocyclyl, optionally substituted with $(C_1-C_{10})$hydrocarbyl or $(C_1-C_{10})$hydrocarbyloxy.

3. A compound according to claim 1 wherein $R^3$ is heteroaryl optionally substituted with $(C_1-C_6)$hydrocarbyl or phenoxy.

4. A compound according to claim 1 wherein $R^1$, $R^{10}$ and $R^{11}$ are hydrogen.

5. A compound according to claim 4 wherein $R^2$ is hydrogen.

6. A pharmaceutical composition comprising a pharmaceutically acceptable carrier and a compound according to claim 1.

7. A method for treating acute myelogenous leukemia by inhibiting αVβ3 in a subject in need thereof, comprising administering to said subject an inhibitory amount of a compound according to claim 1.

8. A method according to claim 7 wherein for selectively inhibiting αVβ3 is inhibited selectively without activating the αVβ3 receptor.

9. An in vitro method for selectively inhibiting αVβ3 without activating the αVβ3 receptor, said method comprising contacting a tissue containing an αVβ3 receptor with an inhibitory amount of a compound according to claim 1.

10. A compound according to claim 1 wherein $R^3$ is chosen from optionally substituted pyrazole, pyrrole, quinoline, isoquinoline, triazole, imidazole, and pyridine.

11. A compound according to claim 10 wherein $R^3$ is chosen from 4-phenyl-1,2,3-triazol-1-yl, 4-isobutyl-1,2,3-triazol-1-yl, 3-phenyl-1,2,4-triazol-1-yl, 6-methoxypyridin-3-yl, 6-phenoxypyridin-3-yl, and quinolin-3-yl.

* * * * *

UNITED STATES PATENT AND TRADEMARK OFFICE
CERTIFICATE OF CORRECTION

PATENT NO. : 11,192,889 B2
APPLICATION NO. : 16/315093
DATED : December 7, 2021
INVENTOR(S) : Coller et al.

Page 1 of 1

It is certified that error appears in the above-identified patent and that said Letters Patent is hereby corrected as shown below:

In the Claims

Column 64, Line 19: Claim 8, Delete "wherein for selectively inhibiting αVβ3 is" and insert
-- wherein αVβ3 is --

Signed and Sealed this
Twelfth Day of April, 2022

Drew Hirshfeld
*Performing the Functions and Duties of the
Under Secretary of Commerce for Intellectual Property and
Director of the United States Patent and Trademark Office*